US007053119B2

(12) United States Patent
Karin et al.

(10) Patent No.: US 7,053,119 B2
(45) Date of Patent: *May 30, 2006

(54) METHODS FOR IDENTIFYING AND USING IKK INHIBITORS

(75) Inventors: Michael Karin, La Jolla, CA (US); Pankaj Kapahi, Pasadena, CA (US)

(73) Assignees: The Regents of the University of California, Oakland, CA (US); Charterhouse Therapeutics Ltd., Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/376,470

(22) Filed: Feb. 28, 2003

(65) Prior Publication Data

US 2003/0232888 A1    Dec. 18, 2003

Related U.S. Application Data

(63) Continuation of application No. 09/721,380, filed on Nov. 22, 2000, now Pat. No. 6,649,654.

(60) Provisional application No. 60/167,090, filed on Nov. 23, 1999, provisional application No. 60/186,023, filed on Mar. 1, 2000.

(51) Int. Cl.
*A61K 31/215* (2006.01)
*A61K 31/12* (2006.01)
*A61K 31/035* (2006.01)

(52) U.S. Cl. ................................ 514/530; 675/744
(58) Field of Classification Search ................ 514/530, 514/675, 744
See application file for complete search history.

(56) References Cited

U.S. PATENT DOCUMENTS

| 4,559,157 | A | 12/1985 | Smith | 424/401 |
|---|---|---|---|---|
| 4,608,392 | A | 8/1986 | Jacquet | 514/772 |
| 4,683,195 | A | 7/1987 | Mullis | 435/6 |
| 4,683,202 | A | 7/1987 | Mullis | 435/91.2 |
| 4,820,508 | A | 4/1989 | Wortzman | 424/59 |
| 4,938,949 | A | 7/1990 | Borch | 514/476 |
| 4,946,778 | A | 8/1990 | Ladner | 435/69.6 |
| 4,965,188 | A | 10/1990 | Mullis | 435/6 |
| 4,992,478 | A | 2/1991 | Geria | 514/782 |
| 6,180,681 | B1 | 1/2001 | Amici | |
| 6,649,654 | B1 * | 11/2003 | Karin et al. | 514/530 |

FOREIGN PATENT DOCUMENTS

WO    90/13678    11/1990

OTHER PUBLICATIONS

Ausubel et al. (eds.), "Immunology," in *Current Protocols in Molecular Biology*, New York: John Wiley & Sons, Chapter 11 (2000).

Baldwin, "The NF-kappa B and I-kappa B proteins: new discoveries and insights," *Annu Rev Immunol* 14:649-83 (1996).

Barnes and Karin, "Nuclear factor-kappaB: a pivotal transcription factor in chronic inflammatory diseases," *N Engl J Med* 336:1066-71 (1997).

Cole et al., "The EBV-hybridoma technique and its application to human lung cancer," in *Monoclonal Antibodies and Cancer Therapy*, Reisfeld and Sell (eds.), New York: Alan R. Liss pp. 77-96 (1985).

Cote et al., "Generation of human monoclonal antibodies reactive with cellular antigens," *Proc Natl Acad Sci U S A* 80:2026-30 (1983).

Delhase et al., "Positive and negative regulation of IkappaB kinase activity through IKKbeta subunit phosphorylation," *Science* 284:309-13 (1999).

DiDonato et al., "A cytokine-responsive IkappaB kinase that activates the transcription factor NF-kappaB," *Nature* 388:548-54 (1997).

Fukushima et al., "Prostaglandin J2—anti-tumour and antiviral activities and the mechanisms involved," *Eicosanoids* 3:189-99 (1990).

Gilroy et al., "Inducible cyclooxygenase may have anti-inflammatory properties," *Nat Med* 5:698-701 (1999).

Gray et al., "Exploiting chemical libraries, structure, and genomics in the search for kinase inhibitors," *Science* 281:533-8 (1998).

Hirose et al., "Expression and localization of cyclooxygenase isoforms and cytosolic phospholipase A2 in anti-Thy-1 glomerulonephritis," *J Am Soc Nephrol* 9:408-16 (1998).

Huse et al., "Generation of a large combinatorial library of the immunoglobulin repertoire in phage lambda," *Science* 246:1275-81 (1989).

Jiang et al., "PPAR-gamma agonists inhibit production of monocyte inflammatory cytokines," *Nature* 391:82-6 (1998).

Jones et al., "Inhibition of angiogenesis by nonsteroidal anti-inflammatory drugs: insight into mechanisms and implications for cancer growth and ulcer healing," *Nat Med* 5:1418-23 (1999).

(Continued)

Primary Examiner—Kevin E. Weddington
(74) Attorney, Agent, or Firm—Medlen & Carroll, LLP

(57) ABSTRACT

The present invention provides methods and compositions for inhibiting IKK, as well as methods and compositions for identifying compounds with activity as inhibitors of IKK, and methods and compositions for the treatment of diseases and/or conditions wherein IKK is implicated and inhibition of its activity is desired. In addition, the present invention provides methods and compositions for the improving the therapeutic activity of COX2 inhibitors, comprising administering the COX2 to a subject in combination with a compound that inhibits IKK activity. The present invention further provides compositions that comprise compounds that inhibit IKK and COX2.

1 Claim, 14 Drawing Sheets

OTHER PUBLICATIONS

Karin and Delhase, "JNK or IKK, AP-1 or NF-kappaB, which are the targets for MEK kinase 1 action?," *Proc Natl Acad Sci U S A* 95:9067-9 (1998).

Kohler and Milstein, "Continuous cultures of fused cells secreting antibody of predefined specificity," *Nature* 256:495-7 (1975).

Kozbor and Roder, "The production of monoclonal antibodies from human lymphocytes," *Immunology Today* 4:72-79 (1983).

Leung et al., "Increased in vitro bone resorption by monocytes in the hyper-immunoglobulin E syndrome," *J Immunol* 140:84-8 (1988).

Maniatis et al., "Regulation of inducible and tissue-specific gene expression," *Science* 236:1237-45 (1987).

Newton et al., "Evidence for involvement of NF-kappaB in the transcriptional control of COX-2 gene expression by IL-1beta," *Biochem Biophys Res Commun* 237:28-32 (1997).

Offenbacher et al., "The use of crevicular fluid prostaglandin E2 levels as a predictor of periodontal attachment loss," *J Periodontal Res* 21:101-12 (1986).

Ricote et al., "The peroxisome proliferator-activated receptor-gamma is a negative regulator of macrophage activation," *Nature* 391:79-82 (1998).

Rossi et al., "2-Cyclopenten-1-one, a new inducer of heat shock protein 70 with antiviral activity," *J Biol Chem* 271:32192-6 (1996).

Rossi et al., "Inhibition of nuclear factor kappa B by prostaglandin A1: an effect associated with heat shock transcription factor activation," *Proc Natl Acad Sci U S A* 94:746-50 (1997).

Rothwarf et al., "IKK-gamma is an essential regulatory subunit of the IkappaB kinase complex," *Nature* 395:297-300 (1998).

Sambrook et al., *Molecular Cloning A Laboratory Manual*, New York: Cold Spring Harbor Laboratory Press pp. 7.39-7.52, 9.31-9.58, & 16.7-16.8,(1989).

Santoro et al., "Prostaglandin A compounds as antiviral agents," *Science* 209:1032-4 (1980).

Santoro et al., "Prostaglandins with antiproliferative activity induce the synthesis of a heat shock protein in human cells," *Proc Natl Acad Sci U S A* 86:8407-11 (1989).

Santoro et al., "Antiviral activity of cyclopentenone prostanoids," *Trends Microbiol* 5:276-81 (1997).

Serhan et al., "Lipid mediator networks in cell signaling: update and impact of cytokines," *FASEB J* 10:1147-58 (1996).

Staels et al., "Activation of human aortic smooth-muscle cells is inhibited by PPARalpha but not by PPARgamma activators," *Nature* 393:790-3 (1998).

Tanaka et al., "Embryonic lethality, liver degeneration, and impaired NF-kappa B activation in IKK-beta-deficient mice," *Immunity* 10:421-9 (1999).

Yamaoka et al., "Complementation cloning of NEMO, a component of the IkappaB kinase complex essential for NF-kappaB activation," *Cell* 93:1231-40 (1998).

Yin et al., "The anti-inflammatory agents aspirin and salicylate inhibit the activity of I(kappa)B kinase-beta," *Nature* 396:77-80 (1998).

Zandi et al., "Direct phosphorylation of IkappaB by IKKalpha and IKKbeta: discrimination between free and NF-kappaB-bound substrate," *Science* 281:1360-3 (1998).

Rossi et al., "Anti-inflammatory cyclopentenone prostaglandins are direct inhibitors of IkB kinase," *Nature* 403:103-108 (2000).

* cited by examiner

```
IKKα:   DLG  Y  A  KDVDQG  SLCTSFVG        T  LQ  Y  L  APE
IKKβ:   DLG  Y  A  KELDQG  SLCTSFVG        T  LQ  Y  L  APE
JNK:    DFG  L  A  RTAGTSFFMMTPYVV         T  RY  Y  R  APE
P38α:   DFG  L  A  RH   T DDEMTGYVA        T  RW  Y  R  APE
```

FIG. 6B

METHODS FOR IDENTIFYING AND USING IKK INHIBITORS

This application is a continuation of U.S. patent application Ser. No. 09/721,380, filed on Nov. 22, 2000 now U.S. Pat. No. 6,649,654, which claims the benefit of U.S. Provisional Applications Ser. No. 60/167,090, filed Nov. 23, 1999 and Ser. No. 60/186,023, filed Mar. 1, 2000.

The present invention was made with government support from the National Institutes of Health, Grant No. R01 A143477-02. The United States Government has certain rights in the invention.

FIELD OF THE INVENTION

The present invention provides methods and compositions for the identification and use of IKK inhibitors. In particular, the present invention provides cyclopentenone prostaglandins suitable for use as IKK inhibitors.

BACKGROUND OF THE INVENTION

The rapid and precise control of gene expression via transcription factors is critical to the survival of cells. Depending upon the inducing stimulus, it can be critical to the survival of a cell to have one or more genes rapidly induced, so that the resultant products are active. For example, an inflammatory response stimulated by an injury or infection, results in rapid vasodilation in the injured area and infiltration of effector cells such as macrophages. Vasodilation occurs within seconds or minutes of the response and is due, in part, to the expression of cytokines by cells in the injured region.

The rapid induction of the inflammatory and immune responses requires that the transcription factors involved in regulating such responses be present in the cell in a form that is amenable to rapid activation. Thus, upon exposure to an inducing stimulus, the response can quickly occur. If such transcription factors are not present in a cell in an inactive state, it is necessary to synthesize the factors upon exposure to an inducing stimulus, greatly reducing the speed with which a response can occur.

Regulation of transcription factor activities involved in such rapid gene induction can occur by various mechanisms. For example, in some cases, a transcription factor that exists in an inactive state in a cell can be activated by post-translational modification (e.g., phosphorylation of one or more serine, threonine, or tyrosine residues). Furthermore, the transcription factor can be rendered inactive by association of the factor with a regulatory factor, which, upon exposure to an inducing stimulus, is released from the transcription factor, thereby activating the transcription factor. Alternatively, an inactive transcription factor may have to associate with a second protein in order to produce transcriptional activity.

Rarely, as in the case of glucocorticoids, the inducing stimulus directly interacts with the inactive transcription factor, rendering it active and resulting in the induction of gene expression. However, more often, an inducing stimulus initiates the induced response by interacting with a specific receptor present on the cell membrane or by entering the cell and interacting with an intracellular protein. Furthermore, the signal generally is transmitted along a pathway, for example, from the cell membrane to the nucleus, due to a series of protein interactions. Such signal transduction pathways allow for the rapid transmission of extracellular inducing stimuli, such that appropriate gene expression is rapidly induced.

Although the existence of signal transduction pathways has long been recognized and many of the cellular factors involved in such pathways have been described, the pathways responsible for the expression of many critical responses, including the inflammatory and immune responses, have only been incompletely defined. For example, it is recognized that various inducing stimuli such as viruses and bacteria, activate common arms of the immune and inflammatory response. However, differences in the gene products expressed also are observed, indicating that these stimuli share certain signal transduction pathways, but also induce other pathways unique to the inducing stimulus. Furthermore, since inducing agents such as bacteria and viruses initially stimulate different signal transduction pathways, yet induce the expression of common genes, some signal transduction pathways must converge at a point such that the different pathways activate common transcription factors.

A clearer understanding of the proteins involved in such pathways facilitates descriptions of drug mechanisms of action. For example, such an understanding facilitates the determination of a drug's mechanism of action (e.g., in cases where the drug is known to interfere with gene expression regulated by a particular pathway, but the target of which is unknown). In addition, an understanding of the pathways involved facilitates the identification of defect(s) in the pathway(s) associated with diseases such as cancer. For example, the altered expression of cell adhesion molecules is associated with the ability of a cancer cell to metastasize. However, the critical proteins involved in the signal transduction pathway leading to expression of cell adhesion molecules have not been identified. Thus, there is a need in the art to identify the proteins involved in signal transduction pathways, particularly those proteins that result in the induction of gene products involved in the inflammatory and immune responses. Indeed, despite much research in the field, there remains a need in the art for compositions and methods for treating and/or preventing infectious as well as other diseases, and inflammation.

SUMMARY OF THE INVENTION

The present invention provides methods for identifying compounds with activities that inhibit IKK. In some preferred embodiments, the methods comprise contacting IKK, or a subunit or fragment of IKK with the compound. In some particularly preferred embodiments, the compound interacts with cysteine-179 of the IKK. In alternative embodiments, the method further comprises determining whether the compound interacts with cysteine-179, wherein the interaction with cysteine-179 correlates with activity as an IKK inhibitor.

The present invention also provides methods to prevent and/or treat diseases and/or conditions associated with NFκB. In particularly preferred embodiments, the method involves inhibition of the action of NFκB. The present invention further provides methods for the inhibition of IKK in vitro and in vivo, as well as methods to prevent NFκB activation in an animal. In some preferred embodiments, the animal is a mammal. In particularly preferred embodiments, the mammal is a human.

The present invention also provides methods to improve the therapeutic activity of COX2 inhibitors in animals (e.g., mammals, including but not limited to humans), comprising administering the COX2 inhibitor in combination with a compound that inhibits IKK activity to an animal. It is contemplated that COX2 inhibitors such as celecoxib, or Fecoxib, NS-398, and PD 98059 (Jones et al., Nat. Med., 18:1418–1423 [1999]), will find use with the present invention. The present invention further provides methods to inhibit the activity of IKK in a cell, comprising contacting the cell with a compound that interacts with IKK. In particularly preferred embodiments, the compound interacts with cysteine-179 of IKK.

The present invention further provides compounds, as well as pharmaceutical compositions comprising compounds that inhibit IKK. The present invention also provides pharmaceutical compositions comprising compounds that are COX2 inhibitors. In additional embodiments, the present invention provides pharmaceutical compositions comprising at least one compound that inhibits IKK, a COX2 inhibitor, and a pharmaceutically accepted carrier.

The present invention also provides the use of the compound of formula I, wherein $R_1$ and $R_2$ are each independently selected from hydrogen, $(C_1-C_{12})$alkyl, and $(C_2-C_{12})$alkenyl, wherein the alkyl or alkenyl is optionally substituted with one or more hydroxy, halo, nitro, trifluoromethyl, cyano, NRR, SR, or COOR; each R is independently selected from the group consisting of hydrogen and $(C_1-C_{12})$alkyl; wherein the optional bond (i.e., the "------" bond) is present or absent, provided that when the optional bond is present, $R_1$ is not hydrogen; and n is 0, 1, 2, or 3; or a pharmaceutically acceptable salt thereof.

The present invention further provides methods for the preparation of medicaments for inhibiting IKK and/or NFκB in an animal, and/or for improving the therapeutic activity of a COX2 inhibitor in an animal. In some preferred embodiments, the present invention provides the use of combination therapies. In these embodiments, at least one compound that inhibits IKK and at least one compound that inhibits COX2 are used in combination. In some embodiments, one compound exhibits multiple activities (e.g., the compound inhibits COX2, as well as IKK and/or NFκB, or any combination of these activities). In still further embodiments, the present invention provides methods to prevent NFκB activation in an animal, comprising inhibiting IKK activity in the animal. In particularly preferred embodiments, IKK activity is inhibited by the administration of a compound that interacts with cysteine-179 of IKK, in an amount effective for the inhibition of IKK activity.

The present invention provides methods for the inhibition of IKK, comprising contacting IKK with a compound that interacts with the cysteine at position 179 of IKK. In some embodiments, the contacting is in vitro, while in other embodiments, it is in vivo. In some particularly preferred embodiments, the compound interacts by forming a covalent bond with the cysteine at position 179 of IKK. In other preferred embodiments, the compound is a Michael acceptor. In further preferred embodiments, the compound is selected from the group consisting of cyclopentenones and substituted cyclopentenones. In some particularly preferred embodiments, the compound is a cyclopentenone prostaglandin. In still further preferred embodiments, the compound is selected from the group consisting of α,β-unsaturated ketones, α,β-unsaturated esters, and α,β-unsaturated nitriles. In some alternatively preferred embodiments, the compound is a compound of formula I:

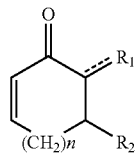

wherein $R_1$ and $R_2$ are each independently selected from hydrogen, $(C_1-C_{12})$alkyl, and $(C_2-C_{12})$alkenyl, wherein the alkyl or alkenyl is optionally substituted with one or more hydroxy, halo, nitro, trifluoromethyl, cyano, NRR, SR, or COOR; each R is independently selected from the group consisting of hydrogen and $(C_1-C_{12})$alkyl; wherein the optional bond is present or absent, provided that when the optional bond (indicated by "--------") is present, $R_1$ is not hydrogen; and n is 0, 1, 2, or 3; or a pharmaceutically acceptable salt thereof. In still further particularly preferred embodiments the compound is selected from the group consisting of $PGA_1$, 15-deoxy-$\Delta^{12-14}PGJ_2$, and pharmaceutically acceptable salts thereof.

The present invention also provides methods for identifying a compound with activity as an inhibitor of IKK, comprising: providing an IKK, wherein the IKK is selected from the group consisting of full-length IKK, subunits of IKK, and fragments of IKK, wherein the IKK comprises a cysteine at position 179, and a test compound; exposing the IKK to the test compound; and determining whether the compound interacts with the cysteine at position 179 of IKK. In some preferred embodiments, the interaction with the compound and the cysteine at position 179 of IKK comprises inhibiting IKK. In some particularly preferred embodiments, the compound interacts with the cysteine at position 179 of IKK by forming a covalent bond with the cysteine at position 179 of IKK.

The present invention further provides methods to improve the therapeutic activity of a COX2 inhibitor in animal, comprising administering a COX2 inhibitor in combination with a compound that inhibits IKK activity to an animal. In some embodiments, the compound is a Michael acceptor. In alternative embodiments, the compound is selected from the group consisting of cyclopentenones and substituted cyclopentenones. In some particularly preferred embodiments, the compound is a cyclopentenone prostaglandin. In further preferred embodiments, the compound is an α,β-unsaturated carbonyl compound. In additional particularly preferred embodiments, the compound is selected from the group consisting of α,β-unsaturated ketones, α,β-unsaturated esters, and α,β-unsaturated nitrites. In still further particularly preferred embodiments, the compound is a compound of formula 1:

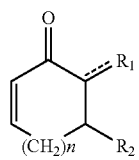

wherein $R_1$ and $R_2$ are each independently selected from hydrogen, $(C_1-C_{12})$alkyl, and $(C_2-C_{12})$alkenyl, wherein the alkyl or alkenyl is optionally substituted with one or more hydroxy, halo, nitro, trifluoromethyl, cyano, NRR, SR, or COOR; each R is independently selected from the group consisting of hydrogen and $(C_1–C_{12})$alkyl; wherein the optional bond (indicated by "------") is present or absent, provided that when the optional bond is present, $R_1$ is not hydrogen; and n is 0, 1, 2, or 3; or a pharmaceutically acceptable salt thereof. In still other particularly preferred embodiments, the compound is selected from the group consisting of $PGA_1$, 15-deoxy-$\Delta^{12-14}$, and pharmaceutically acceptable salts thereof.

The present invention also provides methods to prevent disease associated with NFκB, comprising: providing an animal at risk for disease associated with NFκB, wherein the animal expresses IKK, and a composition that inhibits IKK; and administering the compound to the animal under conditions such that the composition inhibits IKK expressed by the animal, resulting in inhibition of NFκB. In some preferred embodiments, the animal is a human. In additional embodiments, the composition comprises a compound that interacts with cysteine-179 of IKK. In still further embodiments, the disease is selected from the group consisting of inflammation, cancer, bacterial, and viral diseases. In some preferred embodiments, the composition comprises at least one cyclopentenone. In some particularly preferred embodiments, the cyclopentenone is a cyclopentenone prostaglandin.

The present invention further provides methods for the inhibition of IKK, comprising contacting the IKK with a composition that interacts with cysteine-179 of IKK. In some embodiments, the composition interacts with IKK forms a covalent bond with the cysteine-179 of IKK. However, it is not intended that the present invention be limited to this particular type of interaction. In some preferred embodiments, inhibition of IKK results in prevention of NFκB activation.

The present invention also provides methods to treat disease associated with NFκB, comprising: providing an animal having at least one disease associated with NFκB, wherein the animal expresses IKK, and a composition that inhibits IKK; and administering the compound to the animal under conditions such that the composition inhibits IKK expressed by the animal, resulting in inhibition of NFκB. In some preferred embodiments, the animal is a human. In additional preferred embodiments, the composition comprises a compound that interacts with cysteine-179 of IKK. In still further embodiments, the disease is selected from the group consisting of inflammation, cancer, bacterial, and viral diseases. In some preferred embodiments, the composition comprises at least one cyclopentenone. In some particularly preferred embodiments, the cyclopentenone is a cyclopentenone prostaglandin.

DESCRIPTION OF THE FIGURES

FIG. 1A shows the results for Jurkat cells treated with 24 μM $PGA_1$ or diluent for 2 hours and stimulated with TNFα. At the indicated times, cell lysates were prepared and assayed for NF-κB activation by EMSA (electrophoretic mobility shift; upper panel) and IKK activity by kinase assay (KA). The positions of NF-κB:DNA (NF-κB) and non-specific protein:DNA (ns) complexes are indicated. IKK recovery was determined by immunoblotting (IB) for IKKα. No effects of $PGA_1$ (120 μM) on OctI and Sp1 DNA binding activities were observed (right). FIG. 1B shows the results for Jurkat cells treated with 24 μM $PGA_1$ or diluent for 2 hours and stimulated with TPA for the indicated times, after which lysates were prepared and assayed for NF-κB activation (upper panel), IκBα degradation (middle panel) and endogenous IKK activity (bottom panels). FIG. 1C shows the results for the samples described in FIG. 1B, which were analyzed for JNK1 (KA:JNK) and p38 activities. Recoveries of JNK and p38 were determined by immunoblotting. FIG. 1D provides the results for Jurkat cells pretreated with 24 μM $PGA_1$ for the indicated times and stimulated for 15 minutes with TPA. Endogenous IKK and JNK activities and recoveries were determined. FIG. 1E shows the results for HeLa cells pretreated with $PGA_1$ and stimulated for no longer than 10 minutes with TNFα or IL-1. The cell lysates were assayed for endogenous IKK activity and recovery.

FIG. 2A provides results for COS cells transfected with Xpress-tagged NIK (lanes 2–5) and "empty" (lane 1) expression vectors treated with $PGA_1$ (15 μM in Lanes 3 and 4, and 30 μM in lane 5), for either 10 minutes (lane 3), or 18 hours (lanes 4 and 5) after transfection. Cells were lysed and assayed for endogenous IKK activity and recovery 24 hours after transfection. FIG. 2B provides results for COS cells co-transfected with HA-tagged IKKα together with "empty" ("–") or Xpress-tagged NIK ("+") expression vectors, and treated with $PGA_1$ (15 μM in lanes labeled "+"; and 30 μM in lanes labeled "++"), for 10 minutes (lanes 3 and 4) or 18 hours (lanes 5 through 8) after transfection. Cells were lysed and assayed for HA-tagged IKKα associated kinase activity and recovery 24 hours after transfection. FIG. 2C provides results for COS transfected with "empty" (control, lane 1) or HA-tagged IKKβ (lanes 2 through 4) vectors and treated with $PGA_1$ (15 μM, "+"; 30 μM, "++"), at 18 hours after transfection. Cells were lysed and assayed for HA-tagged IKKβ kinase activity and recovery 24 hours after transfection.

FIG. 3A provides results for HeLa cells pretreated with 15 $dPGJ_2$ for 2 hours and left untreated or stimulated with TNFα for 10 minutes. Extracts were assayed for NF-κB binding activity (uppermost panel), IκBα degradation (middle panel), and for endogenous IKK (KA:IKK) and JNK1 (KA:JNK) activities and recoveries (IB:IKKα; IB:JNK). NF-κB and IKK activities were quantified by phosphoimaging and expressed as the percentage of the maximal activity achieved in the absence of the inhibitor. The dose-response curves (bottom panel) represent average results from two separate experiments. FIG. 3B and FIG. 3C provide results for HeLA cells stimulated with TNFα for 15 minutes. IKK was immuno-precipitated and incubated in vitro with the indicated concentrations of $PGA_1$. FIG. 3B provides results for 15 $dPGJ_2$ and FIG. 3C provides results for the diluent, these samples were incubated for 1 hour and kinase assays were conducted (IK:IKK), as well as immunoblots (IB:IKKα). Kinase activity was quantitated by phosphoimaging and used for plotting the dose-response curves.

FIG. 5A provides the results for HeLa cells treated with 50 μM AA, $PGA_1$, $PGB_2$, $PGD_2$, $PGE_1$, $PGE_2$, $PGF_{1α}$, or thromboxane $B_2$ ($TxB_2$), 1 μM $LTB_4$, or 5 μM 15 $dPGJ_2$. FIG. 5B provides the results for 100 μM AA, $PGA_1$, $PGB_2$, $PGD_2$, $PGE_1$, $PGE_2$, $PGF_{1α}$, or $TxB_2$, 2 μM $LTB_4$ or 10 μM 15 $dPGJ_2$.

FIG. 5C provides the structures of the different AA metabolites included in FIG. 5A and FIG. 5B.

FIGS. 6A, 6B, 6C, 6D and 6E provide results indicating that 15 dPGJ$_2$ is a direct inhibitor of IKKβ, whose sensitivity to inhibition is mediated by a cysteine in the activation loop. FIG. 6A provides results that indicate 15 dPGJ$_2$ is not a competitive inhibitor of ATP binding. FIG. 6B provides an alignment of the activation loops of IKKα (SEQ ID NO:1), IKKβ (SEQ ID NO:2), JNK1 (SEQ ID NO:3), and p38α (SEQ ID NO:4). In this Figure, phosphoacceptor sites critical for kinase activation are shown in boldface, while the cysteine residues of IKKα and IKKβ are underlined. FIG. 6C provides results for HeLa cells transiently transfected with expression vectors of IKKβ(wildtype) or IKKβ (C179A) with or without a NIK expression vector. FIG. 6D provides results for Sf9 cells infected with FLAG-tagged wildtype and C179A baculoviruses and incubated with various concentrations of 15 dPGJ$_2$ for 2 hours at 28° C. Following this incubation, the kinase activity and expression were determined.

DEFINITIONS

Figure 1A:
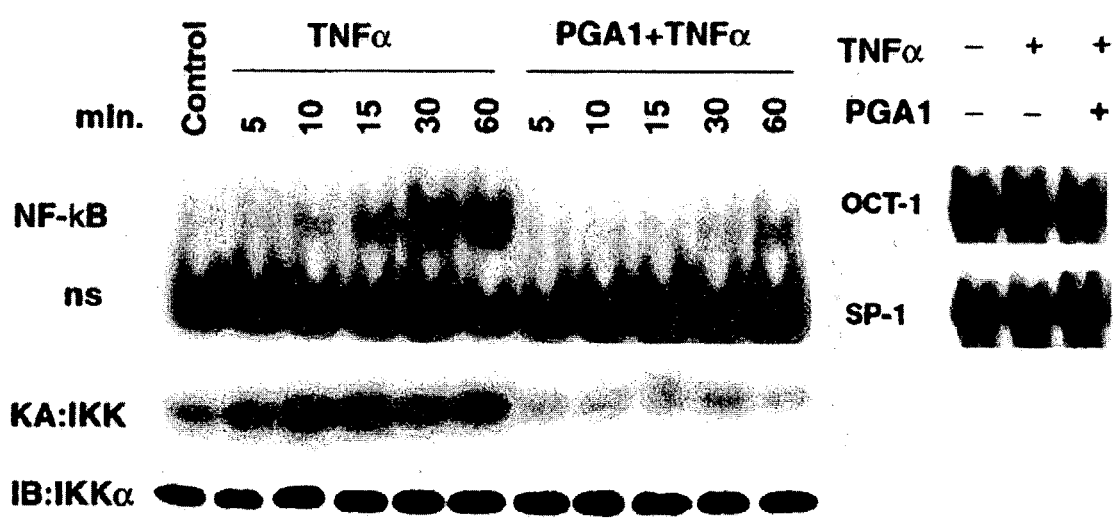
FIGS. 1A, 1B, 1C, 1D and 1E provide results showing the inhibition of TNFα, TPA-induced, and NF-κB activities by $PGA_1$.

To facilitate an understanding of the present invention, a number of terms and phrases are defined below.

As used herein, the term "halo" refers to the halogens (i.e., fluoro, chloro, bromo, and iodo). "Alkyl" and "alkenyl" denote both straight and branched groups. However, reference to an individual radical (e.g., "propyl") encompasses only the straight chain radical, as branched chain isomers (e.g., "isopropyl") are specifically referred to herein.

It is appreciated by those in the art that some of the compounds of the present invention have chiral centers. Such compounds may exist in and be isolated in optically active and racemic forms. In addition, these compounds may exhibit polymorphism. Thus, it is intended that the compounds recited herein encompass any racemic, optically active, polymorphic, or stereoisomeric form, or mixtures thereof. Preparation methods for such optically active forms are also well known in the art (e.g., by resolution of the racemic form by recrystallization techniques, by synthesis from optically-active starting materials, by chiral synthesis, or by chromatographic separation using a chiral stationary phase). Methods for determining anti-inflammatory activity are also well-known in the art (See e.g., Ricote et al., Nature 391:74–82 [1998]; and Gilroy et al., Nature Med., 5:698–701 [1999]).

As used herein, the term "improving the therapeutic activity of a COX2 inhibitor" includes increasing the therapeutic effectiveness of the COX2 inhibitor by a measurable amount over the effectiveness that the COX2 inhibitor would demonstrate if administered in the absence of a compound that inhibits IKK.

Specific and preferred values indicated herein for radicals, substituents, and ranges are for illustrative purposes only. It is not intended that the present invention be so limited. Indeed, these values do not exclude other defined values or other values within defined ranges for the radicals and substituents.

Specifically, (C$_1$–C$_{12}$)alkyl can be methyl, ethyl, propyl, isopropyl, butyl, iso-butyl, sec-butyl, tert-butyl, pentyl, 3-pentyl, iso-pentyl, neopentyl, hexyl, iso-hexyl, hepytl, iso-heptyl, octyl, iso-octyl, sec-octyl, tert-octyl, nonyl, decyl, sec-decyl, undecyl, and dodecyl; and (C$_2$–C$_6$) alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 6-heptenyl, 1-octenyl, 2-octenyl, 3-octenyl, 4-octenyl, 5-octenyl, 6-octenyl, 7-octenyl, 1-noneyl, 2-noneyl, 3-noneyl, 4-noneyl, 5-noneyl, 6-noneyl, 7-noneyl, 8-noneyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl.

Suitable compounds that are effective inhibitors of IKK include, but are not limited to cyclopentenones, substituted cyclopentenones, cyclohexenones, and substituted cyclohexenones. In some embodiments, the cyclopentenone or cyclohexenone is substituted with any suitable group or groups. The only requirement is that the substituted cyclopentenone or cyclopentenone must be an effective inhibitor of IKK.

In one embodiment of the present invention, the compound effectively inhibits IKK in vitro or in vivo, by interacting with cysteine-179 of IKK. In some embodiments, the interaction is electrostatic, while in other embodiments it is by formation of a covalent bond. However, it is not intended that the present invention be limited to these interactions, as any interaction that inhibits NF-κB and/or IKK is encompassed by the present invention.

In some particularly preferred embodiments, the cyclopentenone or substituted cyclopentenone is a cyclopentenone prostaglandin. As used herein, "prostaglandin" refers to any compound or component thereof, which can be derived from unsaturated 20 carbon fatty acids (e.g., arachidonic acid) via the cyclooxygenase pathway. Prostaglandins are a well-known class of extremely potent mediators of a diverse group of physiological processes. It is contemplated that a wide range of cyclopentenone prostaglandins will find use with the present invention.

In other particularly preferred embodiments, the compound that inhibits IKK is a Michael acceptor. As used herein, a "Michael acceptor" refers to any compound that contains a polarized, electrophilic carbon-carbon double bond that is able to reach via a S$_N$2 reaction, with a nucleophilic species (e.g., O$^-$, C$^-$, or S$^-$). Suitable Michael acceptors include α,β-unsaturated carbonyl compounds (e.g., α,β-unsaturated ketones, and α,β-unsaturated esters), and α,β-unsaturated nitriles, although other electron withdrawing substituents (e.g., halo, hydroxy, and nitro) can also activate the carbon-carbon double bond to facilitate nucleophilic attack (See e.g., Carey and Sundberg, *Advanced Organic Chemistry, Part B: Reactions and Synthesis* (2nd ed.), Plenum Press, [1983], pages 31–589, and references cited therein; March, *Advanced Organic Chemistry Reactions, Mechanisms, and Structure*, (2nd ed.), Mc-Graw-Hill Book Co. [1977], pages 549–905, and references cited therein; and Ege, *Organic Chemistry*, Heath and Co. [1984], pages 847–848).

In some embodiments, the α,β-unsaturated ketone is a compound of the formula I:

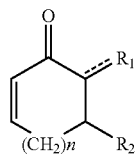

wherein, $R_1$ and $R_2$ are each independently selected from the group consisting of hydrogen ($C_1$–$C_{12}$), and ($C_2$–$C_{12}$) alkenyl, wherein any alkyl or alkenyl is optionally substituted with one or more hydroxy, halo, nitro, trifluoromethyl, cyano, NRR, SR, or COOR, wherein each R is independently selected from hydrogen or ($C_1$–$C_{12}$)alkyl;

the optional bond (represented by "------") is present or absent, with the proviso that when the optional bond is present, $R_1$ is not hydrogen; and n is 0, 1, 2, or 3;

or a pharmaceutically acceptable salt thereof.

In specific embodiments, a value for $R_1$ is selected from the group consisting of hydrogen, ($C_1$–$C_{12}$)alkyl, and ($C_2$–$C_{12}$)alkenyl, optionally substituted with one or more hydroxy groups. In some alternative preferred embodiments, $R_1$ is selected from the group consisting of:

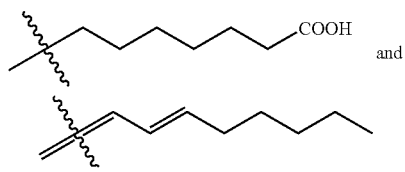

and

In some preferred embodiments, a specific value for $R_2$ is selected from the group consisting of hydrogen, ($C_1$–$C_{12}$) alkyl, or ($C_2$–$C_{12}$)alkenyl, optionally substituted with one or more hydroxy groups. In some preferred embodiments, $R_2$ is selected from the group consisting of:

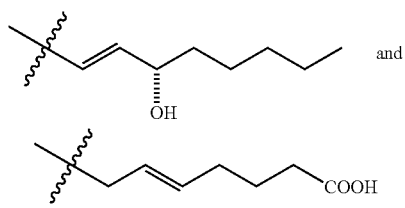

In some particularly preferred embodiments, n is 0, 1, 2, or 3. For example, in some embodiments, n is 0 (i.e., the compound of formula I is a cyclopentenone), while in other embodiments, n is 1 (i.e., the compound of formula I is a cyclohexenone).

In still further embodiments, the compounds of formula I are selected from the 10 group consisting of $PGA_1$ and 15-deoxy-$\Delta^{12-14}PGJ_2$, and pharmaceutically acceptable salts thereof. However, the present invention-is not limited to these specific embodiments.

As used herein, in preferred embodiments, $PGA_1$ is

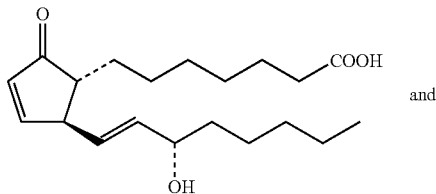

and 15-deoxy-$\Delta^{12-14}PGJ_2$ is

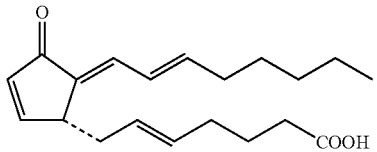

A specific group of compounds useful for inhibiting the actions of NFκB or for treating diseases wherein NFκB is implicated and inhibition of its action is desired is a compound of formula I, wherein n is 1, 2, or 3.

As used herein, the term "inflammation" refers to the tissue response of an organism to an injury.

As used herein, the term "chemical mediator of inflammation" refers to any chemical which is involved in producing, moderating, or terminating the inflammatory response. The term encompasses naturally-occurring, as well as synthetic mediators. The term includes, but is not limited to cytokines and other effector molecules. Indeed, it is intended that the term encompass any molecule or compound that affects the inflammatory response in any aspect or by any mechanism (indeed, an understanding of the mechanism involved is not necessary in order to use the present invention).

As used herein, the term "chemotaxis" refers to the movement of cells in response to a chemical stimulus.

As used herein, the term "leukotaxis" refers to the chemotaxis of leukocytes. In particular, the term refers to the tendency of leukocytes to accumulate in regions of injury and inflammation.

As used herein, the terms "peptide," "polypeptide" and "protein" all refer to a primary sequence of amino acids that are joined by covalent "peptide linkages." In general, a peptide consists of a few amino acids, typically from 2–50 amino acids, and is shorter than a protein. The term "polypeptide" may encompass either peptides or proteins. A peptide, polypeptide or protein may be synthetic, recombinant or naturally occurring. A synthetic peptide is a peptide which is produced by artificial means in vitro (e.g., was not produced in vivo).

The terms "sample" and "specimen" are used in their broadest sense and encompass samples or specimens obtained from any source. As used herein, the term "biological samples" refers to samples or specimens obtained from animals (including humans), and encompasses cells, fluids, solids, tissues, and gases. In preferred embodiments of this invention, biological samples include tissues (e.g., biopsy material), cerebrospinal fluid (CSF), serous fluid, blood, and blood products such as plasma, serum and the like. However, these examples are not to be construed as limiting the types of samples which find use with the present invention.

As used herein, the term "antibody" or "antibodies" refers to any immunoglobulin that binds specifically to an antigenic determinant, and specifically, binds to proteins identical or structurally related to the antigenic determinant which stimulated its production. Thus, antibodies can be used to detect the antigen which stimulated their production. Monoclonal antibodies are derived from a single clone of B lymphocytes (i.e., B cells), and are homogeneous in structure and antigen specificity. Polyclonal antibodies originate from many different clones of antibody-producing cells, and thus are heterogenous in their structure and epitope specificity, but in a population of polyclonals given the same designation, are all directed to the same molecule. Monoclonal and polyclonal antibodies may or may not be purified. For example, polyclonal antibodies contained in crude antiserum may be used in this unpurified state. It is intended that the term "antibody" encompass any immunoglobulin (e.g., IgG, IgM, IgA, IgE, IgD, etc.) obtained from any source (e.g., humans, rodents, non-human primates, caprines, bovines, equines, ovines, etc.).

The antibodies used in the methods invention may be prepared using various immunogens. Such antibodies include, but are not limited to polyclonal, monoclonal, chimeric, single chain, Fab fragments, and an Fab expression library. Various procedures known in the art may be used for the production of polyclonal antibodies. For the production of antibody, various host animals can be immunized by injection with the peptide corresponding to any molecule of interest in the present invention, including but not limited to rabbits, mice, rats, sheep, goats, etc. In one preferred embodiment, the peptide is conjugated to an immunogenic carrier (e.g., diphtheria toxoid, bovine serum albumin (BSA), or keyhole limpet hemocyanin [KLH]). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward molecules of interest in the present invention, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]). In some particularly preferred embodiments of the present invention, the present invention provides monoclonal antibodies of the IgG class.

In additional embodiments of the invention, monoclonal antibodies can be produced in germ-free animals utilizing technology such as that described in PCT/US90/02545. In addition, human antibodies may be used and can be obtained by using human hybridomas (Cote et al., Proc. Natl. Acad. Sci. U.S.A. 80:2026–2030 [1983]) or by transforming human B cells with EBV virus in vitro (Cole et al., in *Monoclonal Antibodies and Cancer Therapy*, Alan R. Liss, pp. 77–96 [1985]).

Furthermore, techniques described for the production of single chain antibodies (See e.g., U.S. Pat. No. 4,946,778; herein incorporated by reference) can be adapted to produce single chain antibodies that specifically recognize a molecule of interest (e.g., at least a portion of IKK, as described herein). An additional embodiment of the invention utilizes the techniques described for the construction of Fab expression libraries (Huse et al., Science 246:1275–1281 [1989]) to allow rapid and easy identification of monoclonal Fab fragments with the desired specificity for a particular protein or epitope of interest (e.g., at least a portion of IKK).

Antibody fragments which contain the idiotype (antigen binding region) of the antibody molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, and the Fab fragments which can be generated by treating the antibody molecule with papain and a reducing agent.

In the production of antibodies, screening for the desired antibody can be accomplished by techniques known in the art (e.g., radioimmunoassay, ELISA [enzyme-linked immunosorbent assay], "sandwich" immunoassays, immunoradiometric assays, gel diffusion precipitin reactions, immunodiffusion assays, in situ immunoassays [e.g., using colloidal gold, enzyme or radioisotope labels], Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

The foregoing antibodies can be used in methods known in the art relating to the localization and structure of compounds such as IKK and/or IKK subunits (e.g., for Western blotting to detect IKKβ), measuring levels thereof in appropriate biological samples, etc. For example, the antibodies can be used to detect proteins of interest in a biological sample from an individual.

The biological samples can then be tested directly for the presence of a protein of interest (e.g., IKK) using an appropriate immunoassay strategy. Alternatively, proteins in the sample can be size separated (e.g., by polyacrylamide gel electrophoresis (PAGE), in the presence (or absence) of sodium dodecyl sulfate (SDS)), and the presence of the protein of interest is then detected by immunoblotting (Western blotting).

The foregoing explanations of particular assay systems are presented herein for purposes of illustration only, in fulfillment of the duty to present an enabling disclosure of the invention. It is to be understood that a variety of immunochemical assay protocols are encompassed within the spirit and scope of the present invention.

The terms "specific binding" or "specifically binding" when used in reference to the interaction of an antibody and a protein or peptide means that the interaction is dependent upon the presence of a particular structure (i.e., the antigenic determinant or epitope) on the protein. In other words, the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

As used herein, the terms "auto-antibody" or "autoantibodies" refer to any immunoglobulin that binds specifically to an antigen that is native to the host organism that produced the antibody (i.e., the antigen is not synthetic and/or has not been artificially supplied to the host organism). However, the term encompasses antibodies originally produced in response to the administration or presence of a foreign and/or synthetic substance in the host, but also cross-react with "self" antigens. The presence of autoantibodies is termed "autoimmunity."

As used herein, the term "antigen" is used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen or portion of an antigen.

The term "antigenic determinant" or "epitope" as used herein refers to that portion of an antigen that makes contact with a particular antibody variable region. When a protein or fragment of a protein is used to immunize a host animal, numerous regions of the protein may induce the production of antibodies which bind specifically to a given region or three-dimensional structure on the protein; these regions or structures are referred to as antigenic determinants.

As used herein, the term "purified" or "to purify" or "purification" refers to the removal or reduction of at least one contaminant from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample (i.e., "enrichment" of an antibody).

The terms "Western blot," "Western immunoblot" "immunoblot" or "Western" refer to the immunological analysis of protein(s), polypeptides or peptides that have been immobilized onto a membrane support. The proteins are first resolved by acrylamide gel electrophoresis to separate the proteins, followed by transfer of the protein from the gel to a solid support, such as nitrocellulose or a nylon membrane. The immobilized proteins are then exposed to an antibody having reactivity towards an antigen of interest. The binding of the antibody (i.e., the primary antibody) is detected by use of a secondary antibody which specifically binds the primary antibody. The secondary antibody is typically conjugated to an enzyme which permits visualization by the production of a colored reaction product or catalyzes a luminescent enzymatic reaction (e.g., ECL reagent, Amersham).

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., *Molecular Cloning: A Laboratory Manual*, Cold Spring Harbor Press, NY, pp 9.31–9.58 [1989]).

The term "Northern blot," as used herein refers to the analysis of RNA by electrophoresis of RNA on agarose gels to fractionate the RNA according to size, followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, J. et al., supra, pp 7.39–7.52 [1989]).

As used herein, the term "ELISA" refers to enzyme-linked immunosorbent assay. Numerous methods and applications for carrying out an ELISA are well known in the art, and provided in many sources (See, e.g., Crowther, "Enzyme-Linked Immunosorbent Assay (ELISA)," in *Molecular Biomethods Handbook*, Rapley et al. [eds.], pp. 595–617, Humana Press, Inc., Totowa, N.J. [1998]; Harlow and Lane (eds.), *Antibodies: A Laboratory Manual*, Cold Spring Harbor Laboratory Press [1988]; and Ausubel et al. (eds.), *Current Protocols in Molecular Biology*, Ch. 11, John Wiley & Sons, Inc., New York [1994]).

In one embodiment of the present invention, a "direct ELISA" protocol is provided, where an antigen is first bound and immobilized to a microtiter plate well. In an alternative embodiment, a "sandwich ELISA" is provided, where the antigen is attached to the stationary phase by capturing it with an antibody that has been previously bound to the microtiter plate well. The ELISA method detects an immobilized antigen by use of an antibody-enzyme conjugate, where the antibody is specific for the antigen of interest, and the enzyme portion allows visualization and quantitation by the generation of a colored or fluorescent reaction product. The conjugated enzymes commonly used in the ELISA include horseradish peroxidase, urease, alkaline phosphatase, glucoamylase or β-galactosidase. The intensity of color development is proportional to the amount of antigen present in the reaction well.

As used herein, the term "in vitro" refers to an artificial environment and to processes or reactions that occur within an artificial environment. In vitro environments consist of, but are not limited to, controlled laboratory conditions. The term "in vivo" refers to the natural environment (e.g., within an organism or a cell) and to processes or reactions that occur within that natural environment.

As used herein, the term "wild-type" refers to a gene or gene product which has the characteristics of that gene or gene product when isolated from a naturally occurring source. A wild-type gene is that which is most frequently observed in a population and is thus arbitrarily designated as the "normal" or "wild-type" form of the gene. In contrast, the term "modified" (or "mutant") refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Nucleic acid sequence," "nucleotide sequence," and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and of non-coding regulatory sequences that do not encode an mRNA or protein product (e.g., promoter sequence, enhancer sequence, polyadenylation sequence, termination sequence, etc.).

"Amino acid sequence," "polypeptide sequence," "peptide sequence," and "peptide" are used interchangeably herein to refer to a sequence of amino acids.

The term "portion" when used in reference to a nucleotide sequence refers to fragments of that nucleotide sequence. The fragments may range in size from 5 nucleotide residues to the entire nucleotide sequence minus one nucleic acid residue. The term "portion" when used in reference to an amino acid sequence refers to fragments of the amino acid sequence. The fragments may range in size from 3 amino acids to the entire amino acid sequence minus one amino acid residue.

An oligonucleotide sequence which is a "homolog" of a first nucleotide sequence is defined herein as an oligonucleotide sequence which exhibits greater than or equal to 50% identity, and more preferably greater than or equal to 70% identity, to the first nucleotide sequence when sequences having a length of 10 bp or larger are compared.

DNA molecules are said to have "5" ends" and "3" ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5" end" if its 5' phosphate is not linked to the 3' oxygen of a mononucleotide pentose ring. An end of an oligonucleotide is referred to as the "3" end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "cloning" as used herein, refers to the process of isolating a nucleotide sequence from a nucleotide library, cell or organism for replication by recombinant techniques.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$° C. to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" the nucleotide sequence portions thereof, will hybridize to its exact complement and closely related sequences.

Low stringency conditions comprise conditions equivalent to binding or hybridization at 68° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5× Denhardt's reagent and 100 μg/ml denatured salmon sperm DNA followed by washing in a solution comprising 0.1×SSPE and 0.1% SDS at 68° C. when a probe of about 100 to about 1000 nucleotides in length is employed.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (see e.g., Anderson and Young, Quantitative Filter Hybridization, in *Nucleic Acid Hybridization* [1985]). Other references include more sophisticated computations which take structural as well as sequence characteristics into account for the calculation of $T_m$.

The term "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined herein as the production of additional copies of a nucleic acid sequence and is generally carried out using polymerase chain reaction technologies well known in the art (see, e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

Transcriptional control signals in eukaryotes comprise "enhancer" elements. Enhancers consist of short arrays of DNA sequences that interact specifically with cellular proteins involved in transcription (Maniatis et al., Science 236:1237 [1987]). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York, pp. 16.7–16.8 [1989]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element," or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

As used herein, the term "subject" refers to any animal, including humans.

As used herein, the term "animal" refers to any animal, including humans, as well as vertebrates such as rodents, non-human primates, ovines, bovines, ruminants, lagomorphs, porcines, caprines, equines, canines, felines, aves, etc.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompass subjects that are experiencing any range of disease, from sub-clinical infection to full-blown disease, wherein the subject exhibits at least some of the indicia (e.g., signs and symptoms) associated with the particular disease.

As used herein, the term "disease" refers to any pathological condition, and encompasses infectious diseases, cancer, and other abnormalities. Indeed, it is not intended that the present invention be limited to any particular disease. In addition, the term encompasses the signs and symptoms associated with pathological processes (e.g., the indicators of inflammation).

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein, the term "kit" is used in reference to a combination of reagents and other materials. It is contemplated that the kit may include reagents such as antibodies, control proteins, as well as testing containers (e.g., microtiter plates, etc.). It is not intended that the term "kit" be limited to a particular combination of reagents and/or other materials.

DESCRIPTION OF THE INVENTION

The ubiquitous NF-κB transcription factor is involved in the activation of an exceptionally large number of genes in response to proinflammatory signals, viral and bacterial infections, and other stressful situations requiring rapid reprogramming of gene transcription. Indeed, NF-κB is a critical activator of genes involved in inflammation and immunity (See e.g., Baldwin, Ann. Rev. Immunol., 14:649–683 [1996]; and Barnes et al., New Engl. J. Med., 336:1066–1071 [1997]). Pro-inflammatory cytokines activate the IκB kinase (IKK complex) that phosphorylates NF-κB inhibitors, triggering their conjugation with ubiquitin and subsequent degradation (See e.g., DiDonato et al., Nature 388:548–554 [1997]; and Zandi et al., Science 281: 1360–1363 [1998]). Freed NF-κB dimers translocate to the nucleus and induce target genes, inlcuding the gene of cyclo-oxygenase 2 (COX2), which catalyzes the synthesis of pro-inflammatory prostaglandins, in particular PGE (See e.g., Herschman et al., Adv. Exp. Med. Biol., 407:61–66 [1997]; and Newton et al., Biochem. Biophys. Res. Comm., 237:28–32 [1997]). However, at the late stages of pro-inflammatory episodes, COX2 directs the synthesis of anti-inflammatory cyclopentenone prostaglandins, indicating a role for these molecules in the resolution of inflammation (See, Gilroy, Nature Med., 5:698–701 [1999]).

Thus, precise regulation of NF-κB transcription factor is important for maintaining good health. Inappropriate regulation of NF-κB transcription factor is directly involved in a wide range of human diseases. In particular, the activation of NF-κB plays an important role in various inflammatory diseases. For example, glucocorticoids inhibit NF-κB by increasing the rate of IκB synthesis, thus, suppressing both immune and inflammatory responses. A large number of viruses, including HIV-1, use NF-κB to mediate viral gene expression. The development of constitutive NF-κB activation appears to be a critical step acquired immune deficiency syndrome (AIDS).

Each of the IκB kinase complexes (IKKs) identified share three common subunits. For example, human serine protein kinase comprises IKKα, IKKβ, and IKKγ subunits. The IKKα and IKKβ subunits possess kinase activity, while the IKKγ subunit is critical for regulating this activity. Proinflammatory signals are known to activate IKKα and IKKβ subunits of IκB. IKKγ interacts directly with IKKα and IKKβ subunits. Reduced IKKγ expression interferes with IκBα phosphorylation and degradation, and thus NF-κB activation. IKKγ can also function to connect the IKK complex to upstream activators.

As mentioned above, pro-inflammatory cytokines can activate the IKK complex. Upon activation, the activated IKK complex (IKB kinase) phosphorylates NF-KB inhibitors (IKB). Free NF-κB dimers produced due to ubiquitination and degradation are then able to translocate to the nucleus of cells and induce target genes, including COX2, which catalyzes the synthesis of pro-inflammatory prostaglandins. The synthesis of pro-inflammatory prostaglandins then results in inflammation. However, as indicated above COX2 also has a role in the resolution of inflammation. In paricular, cyclopentenone prostaglandins have been suggested to exert anti-inflammatory activity through the activation of peroxisome proliferator-activated receptor-γ (See e.g., Ricote et al., Nature 391:79–82 [1998]; and Jiang et al., Nature 391:82–86 [1998]). As discussed in greater detail herein, the present invention provides methods and compositions to reduce and/or prevent inflammation by the inhibition and modification of the IKKβ subunit of IKK. As IKKβ is responsible for the activation of NF-κB by pro-inflammatory stimuli (Dehase et al., Science 284:309–313 [1999]; and Tanaka et al., Immun., 10:421–429 [1999]), the present invention provides means for the utilization of cyclopentenone prostaglandins and improvements in the utilization of COX2 inhibitors.

Cyclopententone Prostaglandins

Cyclopentenone prostaglandins (cyPGs) affect cell proliferation, inhibit inflammation, inhibit NF-κB activation in human cells stimulated with tumor necrosis factor α (TNFα) or 12-O-tetradecanoylphorbol-13-acetate (TPA), and inhibit virus replication (See e.g., Fukushima, Eicosanoids 3:189–199 [1990]; Santoro et al., Proc. Natl. Acad. Sci. USA 86:8407–8411 [1989]; Gilroy et al., Nature Med., 6:698–701 [1999]); Ricote et al., Nature 391:79–82 [1998]; Santoro, Trends Microbiol., 5:276–281 [1997]; Santoro et al., Science 209:1032–1034 [1980]). Cyclopentenone prostaglandins act by activating the heat shock transcription factor HSF, by inhibiting the activation of NF-κB, by blocking IKB degradation, and phosphorylation (See, Santoro et al., Proc. Natl. Acad. Sci. USA 86:8407–8411 [1989]; and Rossi et al., Proc. Natl Acad. Sci., 94:746–750 [1997]). In particular, cyPGs act by preventing phosphorylation and degradation of the NF-κB inhibitor IκBα (Rossi et al., Proc. Natl. Acad. Sci. USA supra). IκBα is phosphorylated by the IKK complex, which contains two catalytic subunits (IKKα and IKKβ) and the IKKγ or NEMO regulatory subunit (Rothwarf et al., Nature 395:297–300 [1990]; and Yamaoka et al., Cell 93:1231–1240 [1998]), at sites that trigger its ubiquitination-dependent degradation (DiDonato et al., Nature 388: 548–554 [1997]; and Zandi et al., Science 281:1360–1363 [1998]).

Figures 1B, 1C:
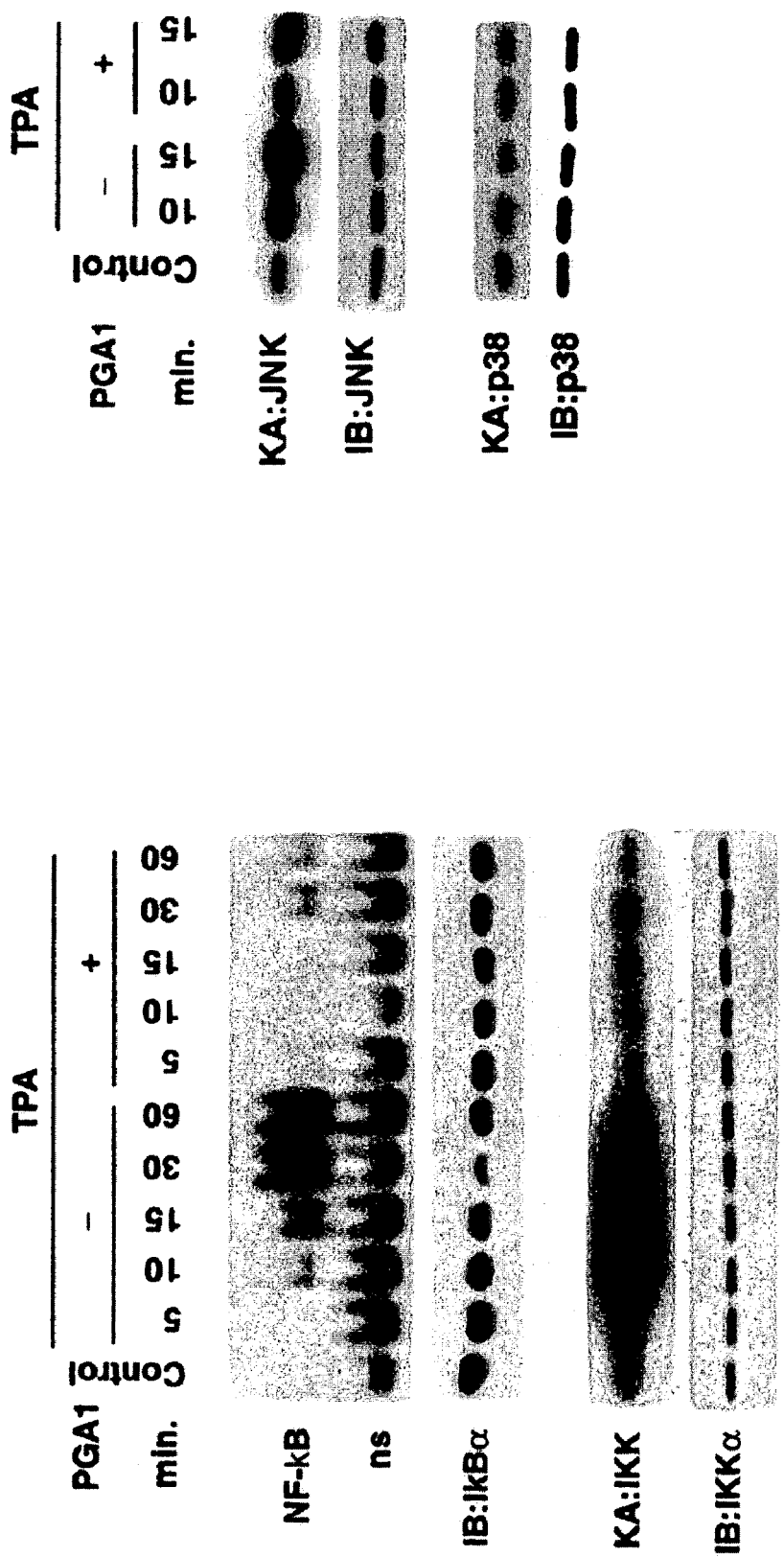
Figures 1D, 1E:
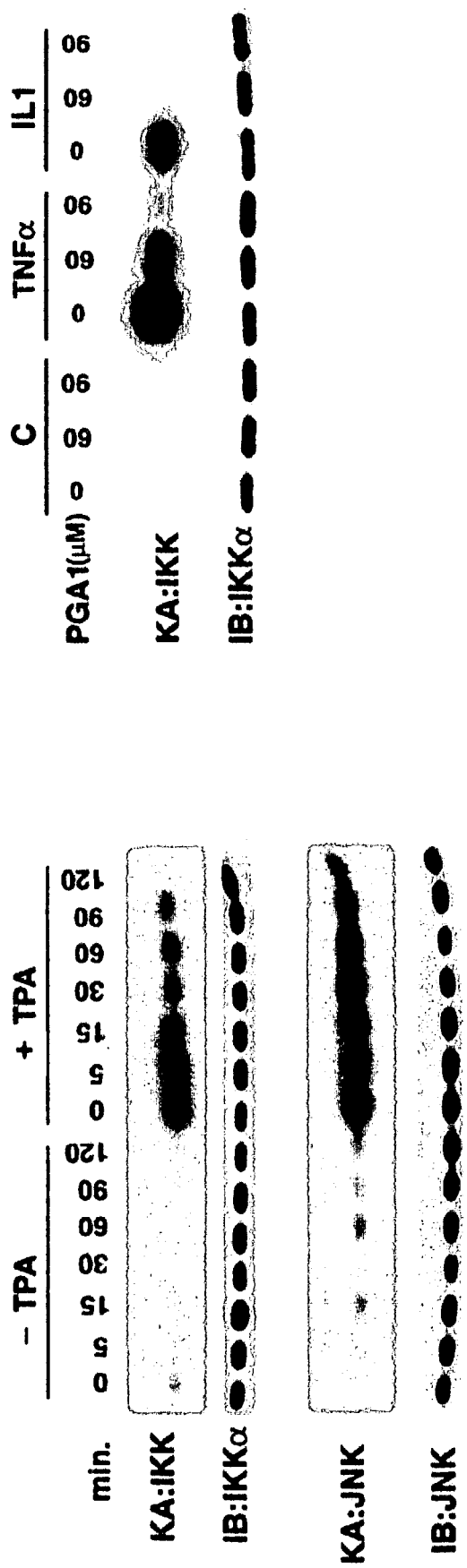

During the development of the present invention, in experiments to determine whether IKK is a target of cyPGs, human lymphoblasoid Jurkat cells were treated with the cyPG prostaglandin $A_1$ ($PGA_1$) and stimulated with either TNFα (i.e., as shown in FIG. 1A), or TPA (i.e., as shown in FIG. 1B). Both TNFα and TPA rapidly stimulated IKK activity, which reached a maximum after 10–15 minutes. $PGA_1$ was shown to inhibit IKK activity and prevent IκBα degradation, as well as NF-κB activation by both inducers (See, FIG. 1A and FIG. 1B), but did not inhibit activation of c-Jun amino-terminal kinases (JNK) and p38 nitrogen-activated protein (MAP) kinases (See e.g., FIG. 1C). Hence, $PGA_1$ targets a selected subset of kinases that activate transcription factors. In addition, $PGA_1$ did not inhibit the DNA binding of transcription factors Oct1 and Sp1 (See e.g., FIG. 1A). A 15-mm exposure to $PGA_1$ was sufficient to partially inhibit IKK activity, but more substantial inhibition required longer pre-incubation (FIG. 1D). Similarly, $PGA_1$ inhibited IKK activity and prevented NF-κB activation in HeLa cells stimulated with interleukin-1 (IL-1) or TNFα (See, FIG. 1E). Thus, the inhibitory effect of $PGA_1$ is independent of type of cell and stimulus. However, the half-maximal inhibitory ($IC_{50}$) concentration of $PGA_1$ towards NF-κB was 12 mM in Jurkat cells, whereas the $IC_{50}$ was 65 mM in HeLa cells (data not shown).

IKK can be activated by the overexpression of protein kinases MEKK1 (MAP kinase Erk kinase kinase 1) or NIK (NF-κB-inducing kinase) (See, Karin and Delhase, Proc. Natl. Acad. Sci. USA 95:9067–9069 [1998]). When added 10 mm or 18 h after the transfection of COS cells with X-press-tagged NIK, $PGA_1$ inhibited activation of endogenous IKK activity (See, FIG. 2A). In a second experiment, COS cells were co-transfected with hemagglutinin A (HA)-tagged IKKα together with either "empty" or NIK vectors. Under the conditions used as described herein, HA-IKKα was incorporated into functional cytokine-responsive complexes with relative molecular mass ($M_r$) 900K (Rothwarf et al., supra). NIK-induced IKK activity was inhibited by $PGA_1$ added immediately after or 18 hours after transfection (FIG. 2B).

$PGA_1$ also inhibited MEKK1-induced IKK activity in Jurkat and in COS cells (data not shown). Of the two catalytic subunits, IKKβ has the major role in responding to pro-inflammatory stimuli (Delhase et al., Science 284:309–313 [1999]; and Tanaka et al., Immun., 10:421–429 [1999]) and is also inhibited by high concentrations of the anti-inflammatory drug aspirin (Yin et al., Nature 398:77–80 [1998]). To determine the effect of cyPG on IKKβ activity, constitutively active IKK complexes were generated, comprising mostly IKKβ homodimers (Zandi et al., supra) by overexpression of HA-tagged IKKβ, in COS cells. In these cells, $PGA_1$ did not affect IKKβ expression, as determined by immunoblotting, whereas it strongly inhibited IKKβ activity (FIG. 2C).

The bioactive cyPG 15-deoxy-$\Delta^{12-14}$-$PGJ_2$ (15 $dPGJ_2$), which is physiologically formed by dehydration and isomerization of the COX metabolite $PGD_2$, can activate peroxisome proliferator-activated receptor-γ (PPAR-γ), a nuclear receptor that interferes with NF-κB transcriptional activity (Ricote et al., supra; and Jiang et al., Nature 391:82–86 [1998]). 15 $dPGJ_2$ inhibits the production of pro-inflammatory cytokines and inducible nitric oxide synthase (iNOS) in activated monocytes by a mechanism suggested to involve PPAR-γ (Ricote et al., supra and Jiang et al., supra).

Figure 3A:
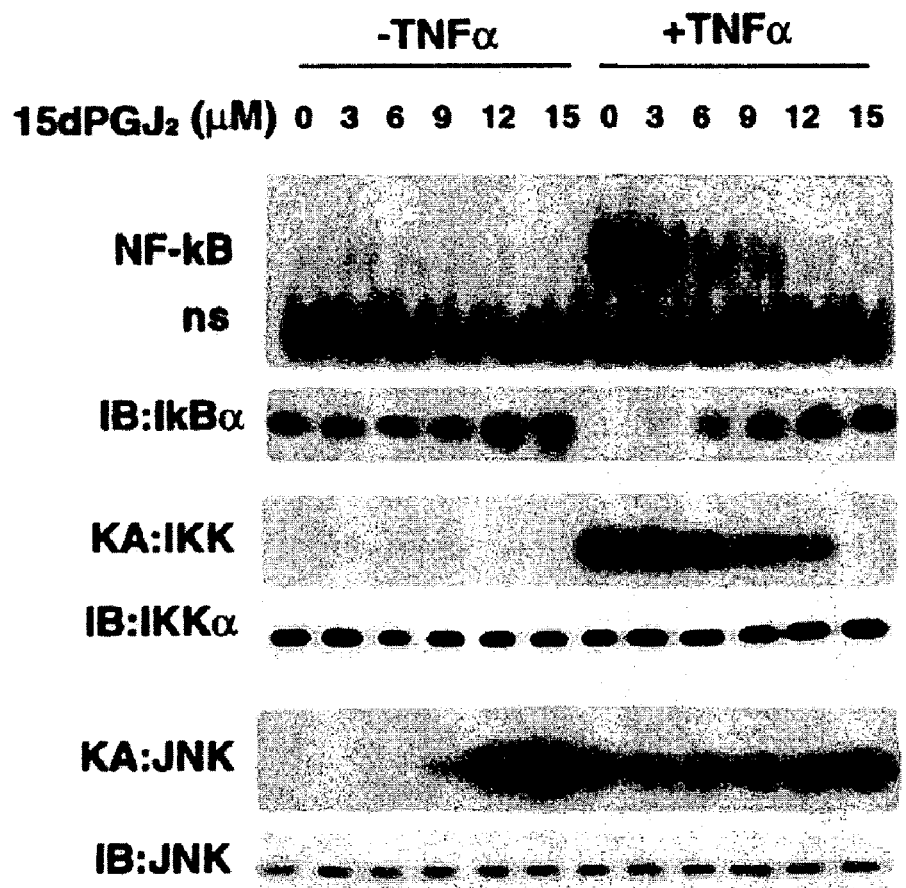
FIGS. 3A, 3B, and 3C provide results showing the inhibition of IKK activity in vivo and in vitro by 15 $dPGJ_2$.
Figure 3A:
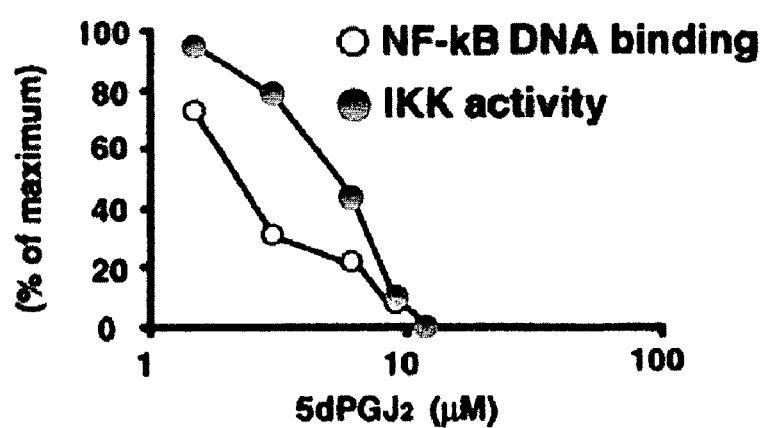

An anti-inflammatory effect of endogenous and exogenous 15 $dPGJ_2$ has been shown in carrageenin-induced pleurisy in rats, which suggests that there is a physiological anti-inflammatory role for cyPGs (Gilroy et al., Nature Med., 5:698–701 [1998]). 15 $dPGJ_2$ was found to be a potent inhibitor of NF-κB activation by TPA in human cells that express very low levels of PPAR-γ (data not shown). Thus, experiments were conducted to examine whether 154 $dPGJ_2$ targets IKK. In HeLa cells, which do not express PPAR-γ (Ricote et al., supra), 15 $dPGJ_2$ inhibited the induction of IKK and NF-κB activities by TNFα (i.e., as shown in FIG. 3A). The $IC_{50}$ for inhibition of NF-κB DNA-binding activity was 2.25 mM, whereas that for IKK activity was 5.08 mM. These concentrations are comparable to those required for inhibition of cytokine synthesis (Ricote et al., supra; and Jiang et al., supra). Intriguingly, 15 $dPGJ_2$ stimulated JNK activity even in the absence of TNFα (See, FIG. 3A). 15 $dPGJ_2$ also inhibited TNFα-induced IKK activity in human peripheral blood monocytes, but did not inhibit the DNA-binding activities of Oct1 or Sp1 (data not shown).

Figure 4:
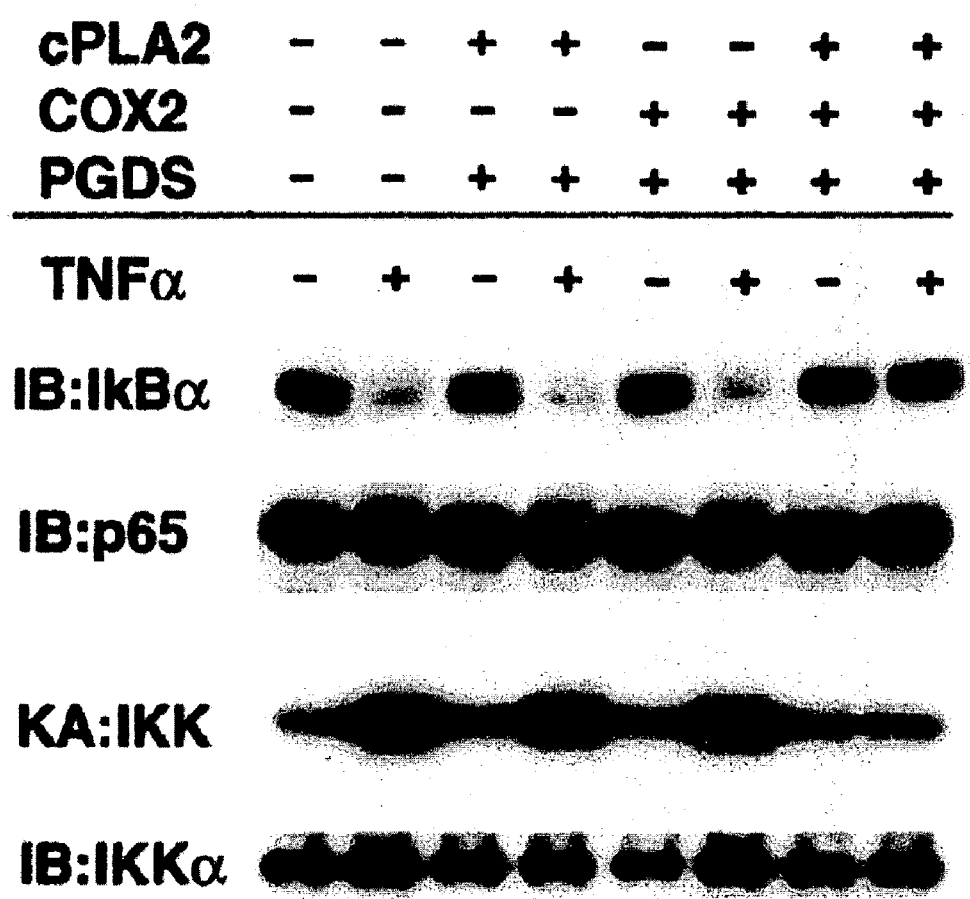
FIG. 4 provides results showing the inhibition of IKK activity through endogenously synthesized PGs (PGD and 15 $dPGJ_2$).

To determine whether endogenous cyPGs are sufficient for inhibition of IKK, 293 cells were transfected with expression vectors for enzymes implicated in biosynthesis of $PGD_2$, which is spontaneously converted to 15 $dPGJ_2$ by non-enzymatic dehydration (Gilroy et al., supra; and Fukushima et al., supra). Combined expression of the arachidonic acid-releasing enzyme cytosolic phospholipase $A_2$ ($cPLA_2$) with COX2 and PGD synthase (PGDS) resulted in the complete inhibition of TNFα-induced IKK activation and IκB phosphorylation and degradation (See, FIG. 4). However, overexpression of each pair of enzymes (i.e., $cPLA_2$/PGDS and COX2/PGDS) was insufficient for inhibition. Thus, levels of cyPG that inhibit IKK can be obtained in vivo.

Only A- and J-type cyPGs inhibited IKK activity in vivo or in vitro. Arachidonic acid and arachidonic acid metabolites including $PGB_2$, $PGD_2$, $PGE_1$, $PGE_2$, $PGF_{1\alpha}$, thromboxane $B_2$ ($TxB_2$) and leukotriene $B_4$ ($LTB$)$_4$ were ineffective (See, FIG. 5A and FIG. 5B). Thus, a reactive α,β-unsaturated carbonyl group in the cyclopentane ring, which renders this portion of the molecule able to form Michael adducts with cellular nucleophilics and covalently modify specific proteins (Fukushima et al., supra; and Rossi et al., J. Biol. Chem., 271:32192–32196 [1996]) is essential for IKK inhibition (See, FIG. 5C). The requirement for a chemically reactive cyclopentenone moiety indicates that cyPGs may inhibit IKKβ through its direct modification. However, an understanding of the mechanism(s) involved is not necessary in order to use the present invention. Nonetheless, while many protein kinase inhibitors compete for ATP-binding sites (Gray et al., Science 281:533–537 [1998]), pre-incubation in the presence of increasing concentrations of ATP had no effect on inhibition of IKKβ by 15 $dPGJ_2$ (See, FIG. 6A). In additional experiments, recombinant IKKβ immobilized on beads was pre-incubated with 15 $dPGJ_2$ or diluent, and rinsed extensively with kinase buffer lacking the inhibitor. Despite extensive washing, the sample that was pre-incubated with 15 $dPGJ_2$ remained inhibited (data not shown). These results indicated that 15 $dPGJ_2$ inhibits IKKβ through direct modification. However, an understanding of the mechanism(s) is not necessary in order to use the present invention.

Nonetheless, cysteine residues are plausible targets for Michael addition reactions on proteins. Both IKKα and IKKβ, but not JNK1 nor p38, contain a cysteine at position 179 within their activation loop (See, FIG. 6B). To examine whether this cysteine is critical for sensitivity to cyPG, site-directed mutagenesis was used to replace it with an alanine. Wild-type IKKβ and IKKβ(C179A) were coexpressed with NIK in HeLa cells, and their sensitivity to 15 $dPGJ_2$ was examined. Although both constructs were equally responsive to NIK, resulting in similar levels of kinase activity, the IKKβ(C179A) mutant was resistant to the inhibitor (See, FIG. 6C). Recombinant IKKβ(C179A) was also resistant to concentrations of 15 $dPGJ_2$ that were inhibitory to wild-type IKKβ (See, FIG. 6D) and also to $PGA_1$ (data not shown).

Also, an NF-κB-dependent transcriptional reporter (2XNFκB-LUC) was co-transfected with an expression vector encoding either wild-type IKKβ or IKKβ(C179A). A NIK expression vector was included to ensure maximal IKK activation. Whereas activation of NF-κB transcription activity through wild-type IKKβ was highly sensitive to 15 $dPGJ_2$, NF-κB activation through IKKβ(C179A) was insensitive to the inhibitor (See, FIG. 6E). Together, these results indicate that cyPGs inhibit IKK by direct modification of its IKKβ subunit. The transfection experiments indicate that IKKβ is the critical target for cyPGs in the NF-κB activation pathway. When IKKβ is rendered resistant to modification, very little inhibition of NF-κB transcriptional activity occurs in cyPG-treated cells.

As indicated previously, CyPGs affect cell proliferation (Fukushima et al., supra; and Santoro et al., Proc. Natl. Acad. Sci. USA 86:8407–8411 [1989]), and inhibit inflammation (Gilroy et al., supra; and Ricote et al., supra), and virus replication (Santoro, Trends Microbiol., 5:276–281 [1997]; and Santoro et al., Science 209:1032–1034 [1980]). Inhibition of NF-κB activation (i.e., a factor that modulates cell proliferation, differentiation and survival, controls inflammation and is required for expression and replication of certain viruses, such as HIV-1) may account for many of these effects. Although inhibition of NF-κB-mediated transcription by cyPG has been attributed to the activation of PPAR-γ, which interferes with NF-κB transcriptional activity (Ricote et al., supra; and Jiang et al., supra), such a mechanism probably requires high levels of PPAR-γ, which are not found in many cell types. In addition, potent PPAR-γ agonists, which are not cyPGs, are poor NF-κB inhibitors (Ricote et al., supra; and Staels et al., Nature 393:79–793 [1998]). In particular, troglitazone, a PPAR-γ agonist, does not inhibit either IKK activity or NF-κB activation in HeLa cells stimulated with TNFα (data not shown).

Although an understanding of the mechanism(s) is not necessary in order to use the present invention, a different, PPAR-γ-independent mechanism that explains the ability of cyPG to inhibit NF-κB is describe herein. Prostaglandins are physiologically present in body fluids at picomolar-to-nanomolar concentrations (See, Fukushima et al., supra; and Serhan et al., FASEB 20:1147–1158 [1996]). However, arachidonic acid metabolism is highly increased in several pathological conditions, including hyperthermia, infection and inflammation (Herschman et al., Adv. Exp. Med. Biol., 407:61–66 [1977]; Newton et al., Biochem. Biophys. Res. Comm., 237:28–32 [1997]; Calderwood et al., J. Cell Physiol., 141:325–333 [1989]; and Leung et al., J. Immunol., 140:84–88 [1988]), and local prostaglandin concentrations in the micromolar range have been detected at sites of acute inflammation (Offenbacher et al., J. Periodontal. Res., 21:101–112 [1986]). Elevated cyPG synthesis has been detected in late phases of inflammation (Ricote et al., supra) and is associated with resolution of inflammation (Gilroy et al., supra). Therefore, concentrations of cyPG that are sufficient for IKK inhibition may occur locally during late phases of inflammatory responses. Moreover, as it is likely that cyPGs inhibit IKK through covalent and irreversible modification, it is contemplated that their effect is cumulative. As COX2 synthesis is under NF-κB control (Herschman et al., supra; and Newton et al., supra), it is contemplated that the inhibition of IKK by cyPGs forms a negative autoregulatory loop that contributes to resolution of inflammation. The results observed during the development of the present invention and described herein, indicate that cyPG, as well as more potent derivatives have therapeutic value in the treatment of inflammatory and viral diseases, as well as certain cancers in which inhibition of NF-κB activity is desirable.

Administration of the Compounds of the Present Invention

As discussed in detail herein, the present invention provides compounds that are effective inhibitors of IKK for the treatment and prevention of disease (or other pathological conditions) in animals (e.g., a mammal such as a human). Such diseases include, but are not limited to chronic and acute inflammation, cancer, viral infection, bacterial infection, and transplant rejection. However, it is not intended that the present invention be limited to any specific disease or condition. Indeed, it is contemplated that the present invention will find use in treatment and/or prevention regimens for numerous diseases and conditions in which inhibition of NF-κB activity is desirable.

In some cases in which the compounds are sufficiently basic or acidic to form stable nontoxic acid or base salts, administration of the compounds as salts is appropriate. Examples of pharmaceutically acceptable salts included but are not limited to organic addition salts formed with acids which form a physiologically acceptable anion, for example, tosylate, methanesulfonate, acetate, citrate, malonate, tartarate, succinate, benzoate, ascorbate, α-ketoglutarate, and α-glycerophosphate. In other embodiments, suitable inorganic salts are formed, including hydrochloride, sulfate, nitrate, bicarbonate, and carbonate salts.

It is contemplated that pharmaceutically acceptable salts for use in the present invention are obtained using standard procedures well known in the art, including but not limited to reacting a sufficiently basic compound such as an amine with a suitable acid, producing a physiologically acceptable anion. Alkali metal (e.g., sodium, potassium, and lithium) or alkaline earth metal (e.g., calcium) salts of carboxylic acids are also contemplated for use in the present invention.

In various embodiments of the present invention, the compounds of formula I are formulated as pharmaceutical compositions and administered to a mammalian host (e.g., humans and other animals), in any of a variety of forms adapted to the chosen route of administration (e.g., orally, intravenous, intramuscular, subcutaneous, topical, etc.). Thus, in some embodiments, the present compounds are systemically administered (e.g., orally or intravenously), in combination with pharmaceutically acceptable vehicle(s) such as an inert diluent or an assimilable edible carrier. In other embodiments, the compounds are enclosed in hard or soft shell gelatin capsules, compressed into tablets, or incorporated directly into or served in conjunction with the subject's diet. In some embodiments for oral therapeutic administration, the active compound is combined with one or more excipients and used in the form of ingestible tablets, buccal tablets, troches, capsules, elixirs, suspensions, syrups, wafers, and the like. In preferred embodiments, such compositions and preparations contain at least 0.1% of active compound. It is contemplated that the percentage of the compositions and preparations will vary, depending upon the particular patient's condition, as known in the art. In some embodiments, the concentration is conveniently formulated to be between about 2 to about 60% of the weight of a given unit dosage form. The amount of active compound in such therapeutically useful compositions is such that an effective dosage level is obtained.

In other embodiments, the tablets, troches, pills, capsules and the like, also contain components such as binders (e.g., gum tragacanth, acacia, corn starch or gelatin), excipients (e.g., dicalcium phosphate); disintegrating agent(s) (e.g., corn starch, potato starch, alginic acid, etc.), lubricant(s) (e.g., magnesium stearate); sweetening agent(s) (e.g., sucrose, fructose, lactose, xylitol, aspartame, etc.), and/or flavoring agent(s) (e.g., peppermint, oil of wintergreen, cherry, etc.). In some embodiments wherein the unit dosage form is a capsule, the capsule contains a liquid carrier (e.g., vegetable oil or polyethylene glycol). Various other materials are also included in some embodiments, including but not limited to coatings (e.g., gelatin, wax, shellac, sugar, etc.), preservatives (e.g., methyl and propylparaben), dyes, etc. In some preferred embodiments, the active compounds are incorporated into sustained release preparations and/or devices. In each of these alternative embodiments, the materials used are pharmaceutically acceptable and substantially non-toxic in the amounts utilized.

In still further embodiments, the active compound(s) is/are administered via injection (e.g., intravenously, intraperitioneally, subcutaneously, intrathecally, intrasynovially, etc.). In these embodiments, solutions of the active compound or its salts are prepared in water and in some embodiments, mixed with nontoxic surfactant(s). In further embodiments, dispersions are prepared in glycerol, liquid polyethylene glycols, triacetin, and mixtures thereof, and in oils. In still further embodiments, the preparations contain preservatives and/or antimicrobials to prevent the growth of microorganisms in the preparation.

Thus, the present invention provides various pharmaceutical dosage forms suitable for injection and/or infusion, including embodiments in which sterile aqueous solutions, dispersions, and/or sterile powders comprising the active ingredient are adapted for the extemporaneous preparation of sterile injectable or infusible solutions or dispersions. In some embodiments, the compositions are encapsulated within liposomes. In all cases, the ultimate dosage form is sterile and stable, under the conditions of manufacture and storage. In some embodiments, the liquid carrier or vehicle is a solvent or liquid dispersion medium (e.g., containing water, ethanol, polyol [e.g., glycerol, propylene glycols, etc.], vegetable oils, nontoxic glyceryl esters, and suitable mixtures thereof). In some embodiments, the proper fluidity is maintained by formation of liposomes, by maintenance of the required particle size (e.g., in dispersions) and/or surfactants. In other embodiments, antimicrobials (e.g., antibacterials and/or antifungals) are incorporated (e.g., parabens, chlorobutanol, phenol, sorbic acid, thimerosal, etc.). In other embodiments, isotonic agents (e.g., sugars, buffers, sodium chloride, etc.), are included. In still further embodiments, prolonged absorption of the injectable compositions is accomplished through use of agent(s) that delay absorption (e.g., aluminum monostearate and gelatin).

In some embodiments, sterile injectable solutions are prepared by incorporating the active compound in the required amount in the appropriate solvent with various additional ingredients (e.g., compositions described above) as required, followed by filter sterilization. In some embodiments utilizing sterile powders for the preparation of sterile injectable solutions, the preferred methods of preparation include, but are not limited to vacuum drying and freeze drying, which yield the active ingredient in powdered form (in addition to any other ingredient(s) present in the previously sterile-filtered solutions).

In some embodiments involving topical administration, dermatologically acceptable carriers (solid or liquid) are utilized. Useful solid carriers include but are not limited to talc, clay, microcrystalline cellulose, silica, alumina, etc. Useful liquid carriers include, but are not limited to water, alcohols, glycols, and/or water-alcohol/glycol blends, in which the active compound(s) are dissolved or dispersed at effective levels, optionally with the aid of non-toxic surfactants. In still further embodiments, other ingredients are also incorporated into the preparation, including but not limited to fragrances. In some embodiments, the compositions of the present invention are applied using absorbent pads, bandages and or dressings impregnated with the composition(s), or sprayed onto the area to be treated using pump or aerosol sprayers.

In still other embodiments, thickeners (e.g., synthetic polymers, fatty acids, fatty acid salts, fatty acid esters, modified celluloses, and modified mineral materials) are employed with liquid carriers, to form spreadable pastes, gels, ointments, soaps, etc., for the direct application of the compositions to the skin. Examples of useful dermatological compositions suitable for use with the present invention include, but are not limited to Jacquet et al. (U.S. Pat. No. 4,608,392), Geria (U.S. Pat. No. 4,992,478), Smith et al., (U.S. Pat. No. 4,559,157), and Wortzman (U.S. Pat. No. 4,820,508), all of which are incorporated herein by reference.

Methods for determining the useful dosages of the compounds of the present invention are known to those in the art. For example, in some embodiments, the useful dosages are determined by comparing the in vitro and in vivo activity in animal models. Methods for extrapolating the effective dosages in mice and other animals to humans are known in the art (See e.g., U.S. Pat. No. 4,938,949, herein incorporated by reference).

It is contemplated that the amount of the compound(s), active salt, or derivative thereof, of the present invention will be determined prior to administration of the compound to a subject to be treated. It is further contemplated that the dosage of the compound(s) will vary, depending upon the condition(s) to be treated, and the age and overall health of the subject. Those of skill in the art are well-familiar with such determinations. However, in general, a suitable dose of the compound (e.g., a compound of formula I), is in the range of from about 0.5 to about 100 mg/kg (e.g., from about 1 to about 75 mg/kg of body weight per day), such as from about 3 to about 50 mg/kg per day, preferably in the range of 5 to 10 mg/kg/day. In particularly preferred embodiments, the compound is conveniently administered in unit dosage form (e.g., containing 5 to 1000 mg, 10 to 750 mg, or 50 to 500 mg of active ingredient per unit dosage form). In alternative particularly preferred embodiments, the active compound is administered so as to achieve peak plasma concentrations of the active compound of from about 0.5 to about 75 µM, preferably, about 1 to 50 1 µM, and most preferably about 2 to about 30 µM. In some embodiments, this is achieved by the intravenous injection of a 0.05% to 5% solution of the active compound. In some embodiments, this is achieved using saline as a diluent (e.g., in injectable embodiments) or orally administering the active compound as a bolus containing about 1–100 mg of the active compound. In some embodiments, desirable blood levels of the active compound are maintained by continuous infusion, so as to provide about 0.01 to 5.0 mg/kg/hr, while in other embodiments, intermittent infusions are used, so as to provide about 0.4 to 15 mg/kg of the active compound.

In addition, in some embodiments, the desired dose is conveniently presented as a single dose, while in other embodiments, multiple doses are provided (e.g., for administration at appropriate intervals during the day, week, or month, etc.). In still other embodiments, the sub-doses are further divided (e.g., into a number of discrete loosely spaced administrations, such as for multiple administrations from an insufflator or by application of a plurality of drops into the eye).

In further embodiments, the ability of the compound(s) of the present invention to inhibit inflammation in particular clinical settings is determined using well-known pharmacological models, in addition (or as an alternative) to the methods described herein (See e.g., Gilroy et al., Nature Med., 5:698–701 [1994]; and Ricote et al., Nature 391: 74–82 [1998]).

Thus, the present invention provides numerous embodiments for the treatment and/or prevention of diseases and/or conditions associated with the NF-κB activity. In particular, the present invention provides methods and compositions suitable to inhibit (prevent or decrease) NF-κB activity.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); BSA (bovine serum albumin); CFA (complete Freund's adjuvant); IFA (incomplete Freund's adjuvant); IgG (immunoglobulin G); IM (intramuscular); IP (intraperitoneal); IV (intravenous or intravascular); SC (subcutaneous); $H_2O$ (water); HCl (hydrochloric acid); wt (wild-type); aa (amino acid); bp (base pair); kb (kilobase pair); kD (kilodaltons); gm (grams); µg (micrograms); mg (milligrams); ng (nanograms); µl (microliters); ml (milliliters); mm (millimeters); nm (nanometers); µm (micrometer); M (molar); mM (millimolar); µM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); FBS and FCS (fetal calf serum); DMEM (Dulbeccomodified Minimum Essential Medium); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris(hydroxymethyl)aminomethane); w/v (weight to volume); v/v (volume to volume); Cayman (Cayman Chemical Co., Ann Arbor, Mich.); Amersham (Arnersham Life Science, Inc. Arlington Heights, Ill.); ICN (ICN Pharmaceuticals, Inc., Costa Mesa, CA); Amicon (Amicon, Inc., Beverly, Mass.); ATCC (American Type Culture Collection, Rockville, Md.); Becton Dickinson (Becton Dickinson Labware, Lincoln Park, NJ); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Qiagen (Qiagen, Inc., Valencia, Calif.); Invitrogen (Invitrogen Corp., San Diego, Calif.); Kodak (Eastman Kodak Co., New Haven, Conn.); New England Biolabs (New England Biolabs, Inc., Beverly, Mass.); Novagen (Novagen, Inc., Madison, Wis.); Pharmacia (Pharmacia, Inc., Piscataway, N.J.); Schleicher & Schuell (Schleicher and Schuell, Inc., Keene, N.H.); Chemicon (Chemicon, Inc., Pittsburgh, Pa.): Sigma (Sigma Chemical Co., St. Louis, Mo.); Sorvall (Sorvall Instruments, a subsidiary of DuPont Co., Biotechnology Systems, Wilmington, Del.); Zymed (Zymed Labs, South San Francisco, Calif.); Jackson ImmunoResearch (Jackson ImmunoResearch Laboratories, Inc., West Grove, Pa.); Stratagene (Stratagene Cloning Systems, La Jolla, Calif.); Whatman (Whatman LabSales, Hillsboro, OR); Ambion (Ambion, Inc., Austin, Tex.); and Zeiss (Carl Zeiss, Inc., Thornwood, N.Y.).

Example 1

Cell Culture, Transfection and Treatments

Cells used in the experiments described herein were cultured in either RPMI 1640 (Jurkat cells) or DMEM (HeLa and COS cells), supplemented with 10% FBS and antibiotics. Cells were stimulated with either 25 ng/ml TPA, 20 ng/ml recombinant TNFα, or 10 ng/ml interleukin 1β (Sigma). $PGA_1$, 15 $dPGJ_2$, $TxB_2$, $LTB_4$, AA and other PGs (Cayman) dissolved in ethanol were used as well, as known in the art (See e.g., Rossi et al., 94:746–750 [1997]). Controls received equal amounts of ethanol. Transfections were performed using Lipofectamine Plus (GIBCO) for HeLa and COS cells and DEAE-dextran (Sigma) for Jurkat cells. Xpress-tagged NIK, Xpress-tagged MEKK1, HA-tagged IKKα, and HA-tagged IKKβ were also used (See e.g., Zandi et al., Science 281:1360–1363 [1998]; and Delhase et al., Science 284:309–313 [1999]). COX2 and cPLA2 expression vectors were obtained from Dr. L. Feng (See also, Hirose et al., J. Am. Soc. Nephrol., 9:408–416 [1998]). PGD synthase was cloned from HT29 colon carcinoma cell line cDNA by PCR and subeloned into a pcDNA3 vector. Cells were lysed in buffer B (50 mM Tris-HCl, pH 7.5, 400 mM NaCl, 1 mM EDTA, 1 mM EGTA, 1% Triton, 0.5% NP-40, 10% glycerol, and supplemented with 20 mM β-glycerophosphate, 10 mM PNPP, 500 mM $Na_3VO_4$, 1 mM PMSF, 20 μg/ml aprotinin, 2.5 μg/ml leupeptin, 8.3 μg/ml bestatin, 1.7 μg/ml pepstatin, and 2 mM DTT).

Example 2

Electrophoretic Mobility Shift Assay (EMSA)

Aliquots of total extracts (15 μg protein) in buffer B were incubated with a $^{32}$P-labeled κB DNA, followed by analysis of DNA-binding activities by EMSA on 4% PAGE gels, as known in the art (See, Rossi et al., supra). Specificity of protein-DNA complexes was verified by supershift with polyclonal antibodies specific for p65 (Rel A).

Example 3

Kinase Assay, Immunoprecipitation and Immunoblotting

Cell lysates were incubated with anti-IKKα (Pharmingen), anti-HA (12CA5; Pharmingen), anti-JNK1 (333.8; Pharmingen), or anti-p38 (New England Biolabs) for 2 hours. Then, 15 μl protein A-Sepharose (Sigma) were added and the mixture was allowed to incubate for 1 hour. After extensive washing, kinase assays were performed as known in the art (See e.g., DiDonato et al., Nature 388:548–554 [1997]). Endogenous IKK, HA-tagged IKKα, endogenous JNK1, and p38 activities were determined with GST-1κBα (1–54), GST-c-Jun(1–79), and GST-ATF2 as substrates.

In addition, recombinant IKKβ was expressed in Sf9 cells and purified as described (Zandi et al., supra). AA, PGs, $LTB_4$, and $TxB_2$ were added to washed immunoprecipitates of recombinant IKKβ in kinase buffer to a final volume of 500 μl. After 1.5 hours at 4° C., the immunoprecipitates were washed and the kinase activity determined. Western blot analysis was also performed as known in the art (See e.g., Rossi et al., supra).

Example 4

Targeting of IKK by Cyclopentenone Prostaglandins

Human lymphoblastoid Jurkat cells were treated with the cyPG prostaglandin $A_1$ ($PGA_1$) and stimulated with either TNFα (as indicated in FIG. 1A) or TPA (as indicated in FIG. 1B). Both TNFα and TPA rapidly stimulated IKK activity, reaching a maximum after 10–15 minutes. As indicated in FIG. 1A and FIG. 1B, $PGA_1$ inhibited IKK activity and prevented IκBα degradation and NF-κB activation by both inducers. However, as indicated in FIG. 1C, $PGA_1$ did not inhibit activation of JNK and p38 MAP kinases. Hence, $PGA_1$ targets a selected subset of kinases that activate transcription factors. In addition, $PGA_1$ did not inhibit DNA binding of transcription factors Oct1 and Sp1, as shown in FIG. 1A. A 15 minute exposure to $PGA_1$ was sufficient to partially inhibit IKK activity, but more substantial inhibition required longer preincubation, as indicated by the results in FIG. 1D. Similarly, $PGA_1$ inhibited IKK activity and prevented NF-κB activation in HeLa cells stimulated with interleukin-1 (IL-1) or TNFa, as indicated in FIG. 1E. Thus, the inhibitory effect of $PGA_1$ is independent of the type of cell and stimulus. However, in Jurkat cells, the half-maximal inhibitory ($IC_{50}$) concentration of $PGA_1$ towards NF-κB was 12 μM, whereas the half-maximal inhibition for HeLa cells was 65 μM $PGA_1$.

Example 5

15 $dPGJ_2$ Targets IKK

Figure 2A:
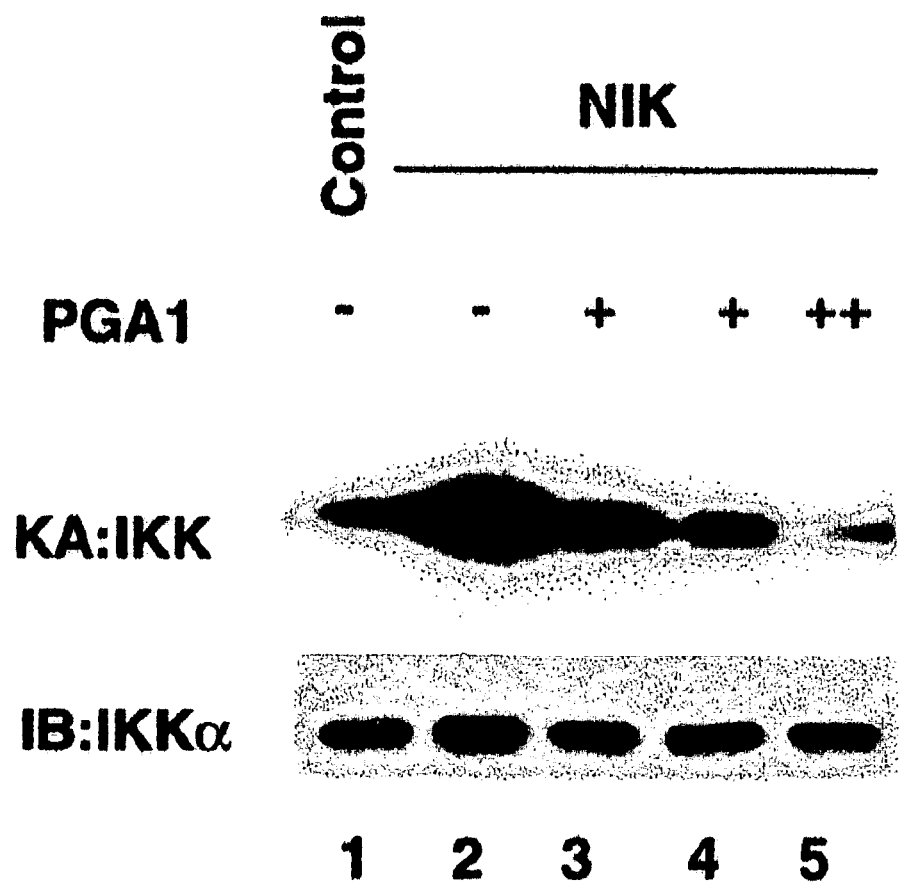
FIGS. 2A, 2B and 2C provide results indicating that $PGA_1$ prevents NIK-induced IKK activation and inhibits IKKβ activity.
Figures 2B, 2C:
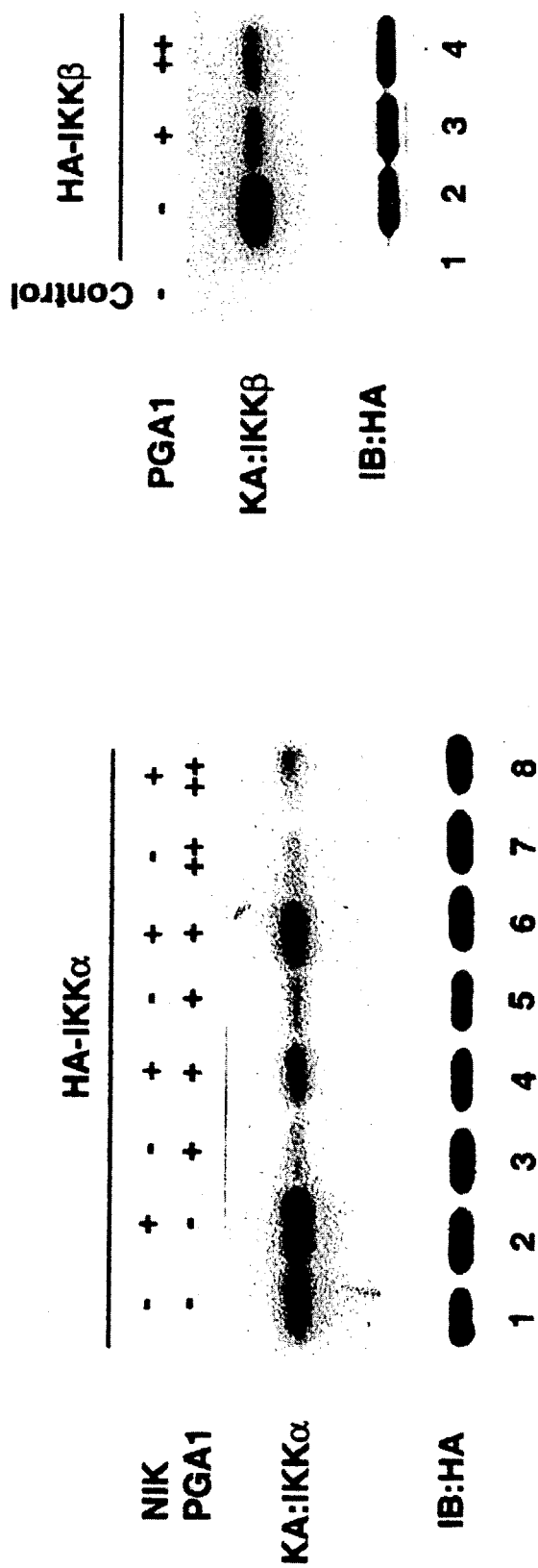

In HeLa cells, which do not express PPAR-γ, 15 $dPGJ_2$ inhibited induction of IKK and NF-κB activities by TNFα, as shown in FIG. 2A. The $IC_{50}$ for inhibition of NF-κB DNA binding activity was 2.25 μM, while the half-maximal inhibition of IKK activity was observed to be 5.08 μM for 15 dPGJ$_2$. These concentrations are comparable to those required for inhibition of cytokine synthesis. 15 dPGJ$_2$ stimulated JNK activity, even in the absence of TNFα, as indicated in FIG. 2A. 15 dPGJ$_2$ also inhibited TNFα-induced IKK activity in human peripheral blood monocytes and did not inhibit Oct1 nor Sp1 DNA binding activities.

Example 6

Cyclopentenone Prostaglandins Inhibit IKK Activity In Vitro

Endogenous IKK was immunoprecipitated from TNFα-stimulated HeLa cells and the kinase activity determined in the presence of different concentrations of PGA$_1$ (the results of which are shown in FIG. 2B) or 15 dPGJ$_2$ (the results of which are shown in FIG. 2C). IKK activity was inhibited in a dose-dependent fashion by both PGA$_1$ and 15 dPGJ$_2$, with IC$_{50}$ values of 79.8 µM and 7.08 µM, respectively. No significant inhibition of either p38 or JNK1 activities was observed upon in vitro incubation with up to 60 µM 15 dPGJ$_2$.

Example 7

Levels of Cyclopentenone Prostaglandins That Inhibit IKK can be Obtained In Vivo In these experiments, HEK 293 cells were transfected with expression vectors encoding enzymes implicated in the biosynthesis of PGD$_2$, which is spontaneously converted to 15 dPGJ$_2$ by non-enzymatic degradation. Briefly, HEK 293 cells were transfected with expression vectors for cytosolic phospholipase A2 (cPLA2), cyclooxygenase 2 (COX2), and prostaglandin D synthase (PGDS). After 12 hours, the cells were washed, incubated in low serum (0.5%) medium for an additional 30 hours and then treated with TNFα for 15 minutes. IκBα degradation and IKK activity were then determined. IκBα immunoblots were reprobed with anti-p65, to verify equal loading of samples.

Figures 3B, 3C:
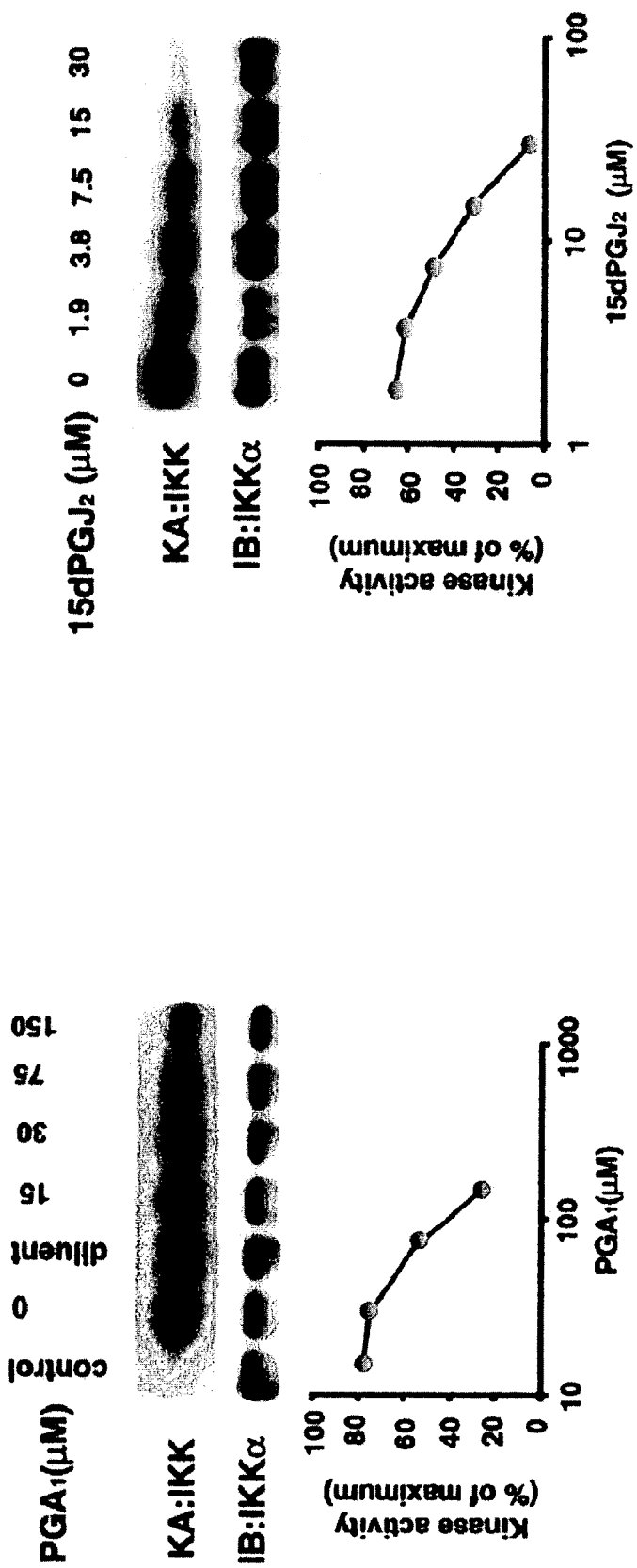

As indicated in FIG. 3A, 3B and 3C, combined expression of the arachidonic acid (AA) releasing enzyme cytosolic phospholipase (cPLA2) with COX2 and PGD synthase (PGDS) resulted in complete inhibition of TNFα-induced IKK activation and IκB phosphorylation and degradation. However, overexpression of each pair of enzymes (i.e., cPLA2+PGDS and COX2+PGDS) was insufficient for inhibition.

Example 8

A and J Type Cyclopentenone Prostaglandins are Effective Inhibitors of IKK

Figure 5B:
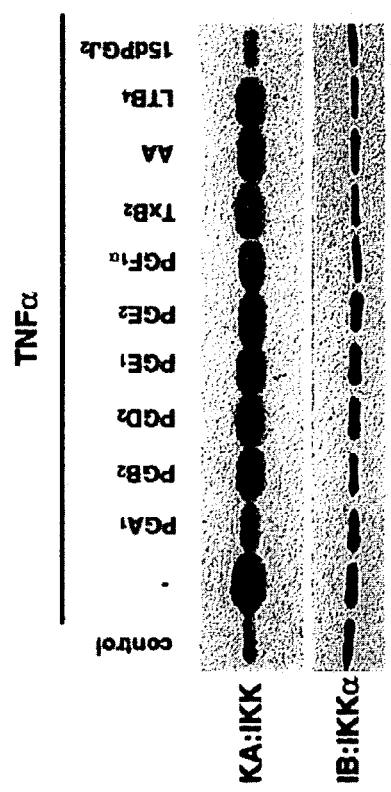
FIGS. 5A, 5B and 5C provide the results of experiments to determine the effect of arachidonic acid and its inetabo-lites on IKK activity in vivo and in vitro.
Figure 5A:
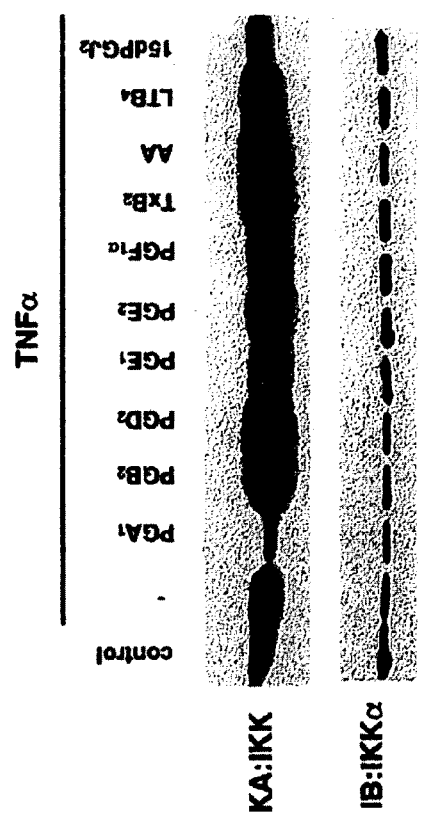
Figure 5C:
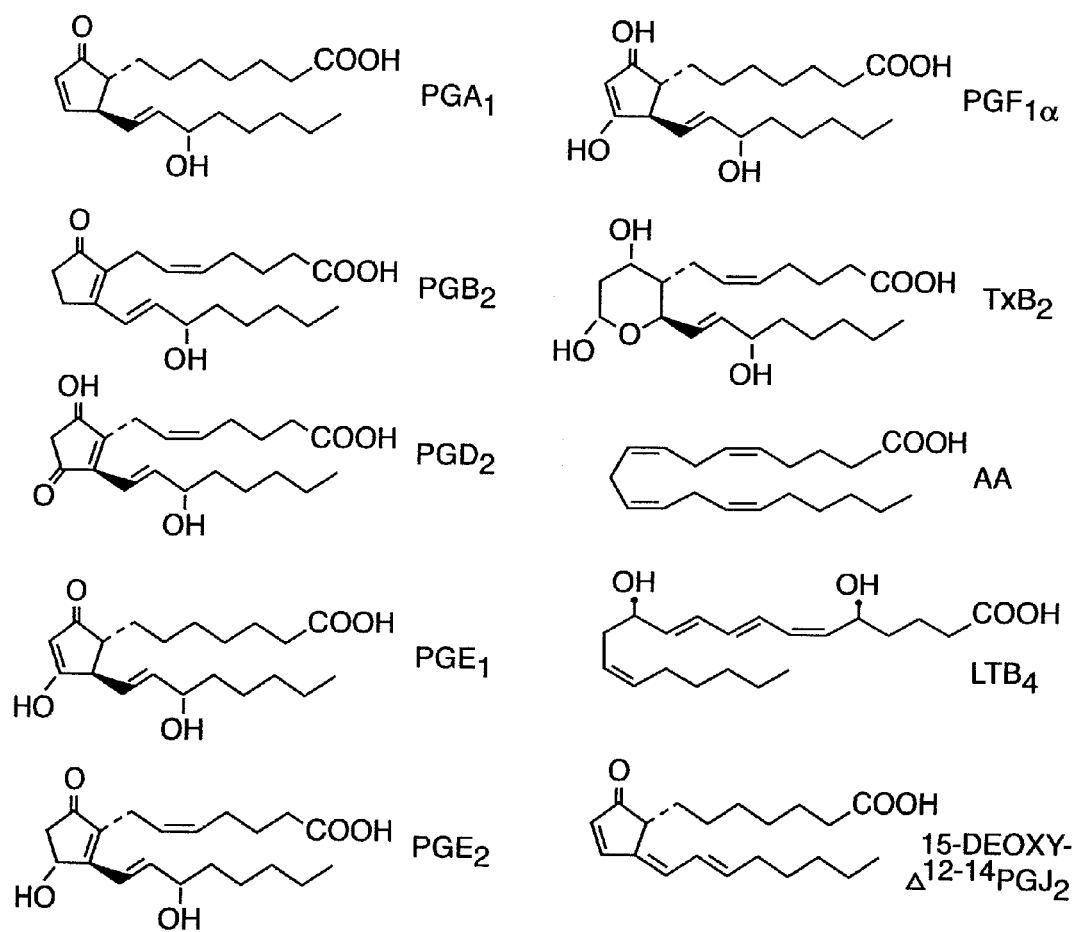

In this Example, experiments to determined the effects of arachidonic acid and its metabolites on IKK activity in vivo and in vitro are described. HeLa cells were treated with 50 µM AA, PGA$_1$, PGB$_2$, PGD$_2$, PGE$_1$, PGE$_2$, PGF$_{1\alpha}$, or thromboxane B$_2$ (TxB$_2$), 1 µM LTB$_4$, or 5 µM 15 dPGJ$_2$, for 2 hours in RPMI containing 10% FCS, and stimulated with TNFα for 10 minutes. Cell lysates were then assayed for endogenous IKK activity and recovery. These results are shown in FIG. 5A. In this Figure, "control" indicates unstimulated cells, and "−" indicates treatment with diluent alone. In addition, IKK was immunoprecipitated from TNFα-stimulated HeLA cells and incubated in vitro with 100 µM AA, PGA$_1$, PGB$_2$, PGD$_2$, PGE$_1$, PGE$_2$, PGF$_{1\alpha}$, or TxB$_2$, 2 µM LTB$_4$ or 10 µM 15 dPGJ$_2$, followed by kinase assay and immunoblot analysis. These results are shown in FIG. 5B. In this Figure, "control" indicates to unstimulated cells, and "−" indicates 1% ethanol. FIG. 5C shows the structure of the different AA-metabolites used in these experiments and indicated in FIG. 5A and FIG. 5B.

Type A and J cyPGs were found to inhibit IKK activity in vivo and in vitro. In contrast, AA and AA metabolites, including PGB$_2$, PGD$_2$, PGE$_1$, PGE2, PGF$_{1\alpha}$, thromboxane B$_2$ (TxB$_2$) and leukotriene B$_4$ (LTB$_4$) were ineffective. The results in FIG. 5A and FIG. 5B, indicate that the presence of a reactive α,β-unsaturated carbonyl group in the cyclopentane ring, which renders this portion of the molecule able to form Michael adducts with cellular nucleophilics and covalently modify specific proteins, is essential for IKK inhibition (See e.g., FIG. 5C).

Example 9

15 dPGJ$_2$ May Inhibit IKK Through Direct Modification

Figure 6A:
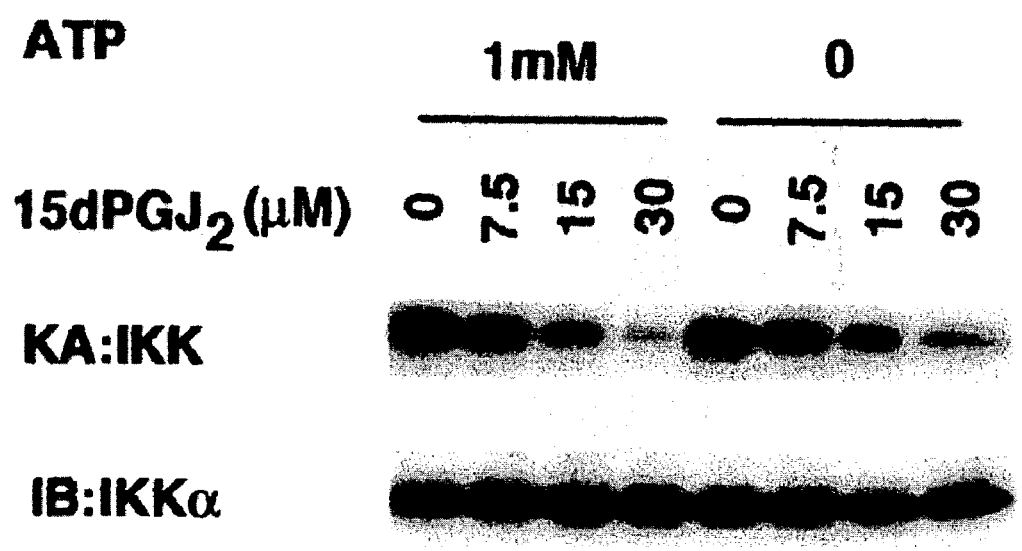

The requirement for a chemically reactive cyclopentenone moiety suggested that cyPGs inhibit IKKβ through direct modification. Many protein kinase inhibitors compete with binding of ATP, but preincubation in the presence of increasing concentrations of ATP had no effect on inhibition of IKKβ by 15 dPGJ$_2$, as indicated in FIG. 6A. FIG. 6A shows results for IKK immunoprecipitated from TNFα stimulated HeLa cells and incubated with 15 dPGJ$_2$ (0–30 µM) with or without ATP in lysis buffer at 4° C. for 30 minutes. The pellets were rinsed and kinase activity was measured.

In other experiments, purified recombinant IKKβ immobilized on beads with 15 dPGJ$_2$ or diluent were preincubated and extensively rinsed with kinase buffer lacking the inhibitor. Despite extensive washing, the sample that was preincubated with 15 dPGJ$_2$ remained inhibited. These results indicate that 15 dPGJ$_2$ may inhibit IKKβ through direct modification.

Although an understanding of the mechanism(s) are not necessary in order to use the present invention, cysteine residues are plausible targets for Michael addition reactions on proteins. Both IKKβ and IKKα, but not not JNK1 nor p38, contain a cysteine at position 179 within their active loop (See, FIG. 6B; Ricote et al., Nature 391:74–82 [1998]).

In an experiment to determine whether this cysteine is critical for sensitivity to cyPG, cysteine was replaced with an alanine using site-directed mutagenesis. In these experiments, HeLa cells were transiently transfected with expression vectors for IKKβ(WT) or IKKβ(C179A) with or without a NIK expression vector. After 16 hours, NIK transfected cells were treated for 2 hours with 15 dPGJ$_2$. Kinase activity (KA) and expression (IB:HA) were subsequently determined. Thus, wild-type (WT) IKKβ and mutant IKKβ (i.e., IKKβ (C179A)) were coexpressed with NIK in HeLa cells and their sensitivity to 15 dPGJ$_2$ examined. While both constructs were equally responsive to NIK, resulting in similar levels of kinase activity, the IKKβ(C179A) mutant was resistant to inhibitor (See, FIG. 6C).

Figures 6C, 6D:
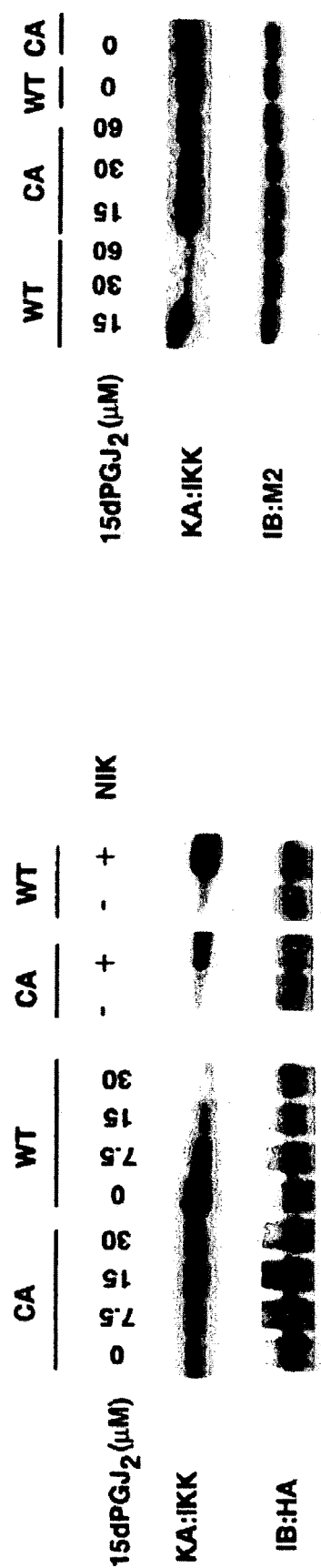
Figure 6E:
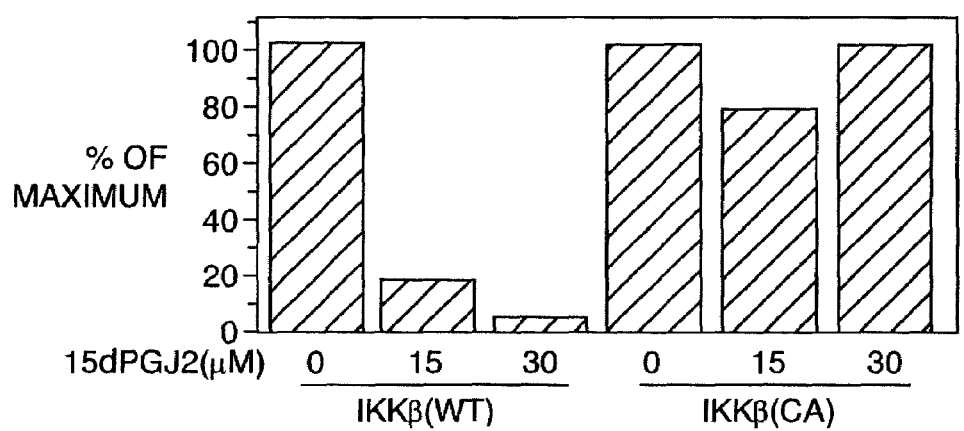

Recombinant IKKβ(C179A) was also resistant to concentrations of 15 dPGJ$_2$ that were inhibitory to wild-type IKKβ (as shown in FIG. 6D), and also to PGA$_1$. An NF-κB dependent transcriptional reporter (2XNFκB-LUC) was pre-incubated with expression vector encoding either wild-type IKKβ or IKKβ(C179A). A NIK expression vector was included to ensure maximal IKK activation. While activation of NF-κB transcriptional activity through wild-type IKKβ was highly sensitive to 15 dPGJ$_2$, NF-κB activation through IKKβ(C179A) was insensitive to the inhibitor (See, results shown in FIG. 6E). FIG. 6E provides the results for HeLa cells transiently transfected with a 2xNF-κB-LUC reporter, a NIK expression vector and expression vectors for wild type IKKβ or IKKβ(C179A). At 3 hours post-transfection, cells were treated with 15 dPGJ$_2$ and at 24 hours, the luciferase activities were determined for duplicate samples. In each case, the maximal activity achieved in the absence of inhibitor was given an arbitrary value of 100% and the other values were calculated relative to this one.

Collectively, these results strongly indicate that cyPGs inhibit IKK by direct modification of the IKKβ subunit. In addition, the transfection experiments indicate that IKKβ is the critical target for cyPGs in the NF-κB activation pathway. When IKKβ is rendered resistant to modification, very little inhibition of NF-κB transcriptional activity occurs in cyPG-treated cells.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and/or related fields are intended to be within the scope of the following claims.

The invention claimed is:

1. A method for the inhibition of IκB kinase (IKK), comprising contacting IKK with a compound that interacts with the cysteine at position 179 of IKKbeta, wherein said compound is selected from the group consisting of $PGA_1$, 15-deoxy-$\Delta^{12-14}PGJ_2$, and pharmaceutically acceptable salts thereof.

* * * * *

UNITED STATES PATENT AND TRADEMARK OFFICE
CERTIFICATE OF CORRECTION

PATENT NO.        : 7,053,119 B2                                              Page 1 of 1
APPLICATION NO.   : 10/376470
DATED             : May 30, 2006
INVENTOR(S)       : Karin et al.

It is certified that error appears in the above-identified patent and that said Letters Patent is hereby corrected as shown below:

On the Title Page,

Item (75) Inventors: should read as follows:

Inventors: Michael Karin, La Jolla, CA (US);
Pankaj Kapahi, Pasadena, CA (US);
Maria Gabriella Santoro, Avellino, Italy (IT)

Signed and Sealed this

Twenty-first Day of November, 2006

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 27
<212> TYPE: PRT
<213> ORGANISM: Artificial Sequence
<220> FEATURE:
<223> OTHER INFORMATION: Synthetic

<400> SEQUENCE: 1

Asp Leu Gly Tyr Ala Lys Asp Val Asp Gln Gly Ser Leu Cys Thr Ser
1               5                   10                  15

Phe Val Gly Thr Leu Gln Tyr Leu Ala Pro Glu
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic

<400> SEQUENCE: 2

Asp Leu Gly Tyr Ala Lys Glu Leu Asp Gln Gly Ser Leu Cys Thr Ser
1               5                   10                  15

Phe Val Gly Thr Leu Gln Tyr Leu Ala Pro Glu
            20                  25

<210> SEQ ID NO 3
<211> LENGTH: 28
<212> TYPE: PRT
<213> ORGANISM: Artificial Sequence
<220> FEATURE:
<223> OTHER INFORMATION: Synthetic

<400> SEQUENCE: 3

Asp Phe Gly Leu Ala Arg Thr Ala Gly Thr Ser Phe Phe Met Met Thr
1               5                   10                  15

Pro Tyr Val Val Thr Arg Tyr Tyr Arg Ala Pro Glu
            20                  25

<210> SEQ ID NO 4
<211> LENGTH: 25
<212> TYPE: PRT
<213> ORGANISM: Artificial Sequence
<220> FEATURE:
```

```
<223> OTHER INFORMATION: Synthetic

<400> SEQUENCE: 4

Asp Phe Gly Leu Ala Arg His Thr Asp Asp Glu Met Thr Gly Tyr Val
1               5                   10                  15

Ala Thr Arg Trp Tyr Arg Ala Pro Glu
            20                  25
```